(12) United States Patent
Thompson et al.

(10) Patent No.: US 7,087,419 B2
(45) Date of Patent: Aug. 8, 2006

(54) DNA ENCODING A PLANT LIPASE, TRANSGENIC PLANTS AND A METHOD FOR CONTROLLING SENESCENCE IN PLANTS

(75) Inventors: John E. Thompson, Waterloo (CA); Tzann-Wei Wang, Waterloo (CA); Katalin Hudak, East Brunswick, NJ (US); Yuwen Hong, Waterloo (CA)

(73) Assignee: Senesco, Inc., New Brunswick, NJ (US)

( * ) Notice: Subject to any disclaimer, the term of this patent is extended or adjusted under 35 U.S.C. 154(b) by 324 days.

(21) Appl. No.: 10/674,540

(22) Filed: Oct. 1, 2003

(65) Prior Publication Data

US 2004/0158891 A1 Aug. 12, 2004

Related U.S. Application Data

(63) Continuation of application No. 09/610,104, filed on Jul. 5, 2000, now Pat. No. 6,774,284, which is a continuation-in-part of application No. 09/597,774, filed on Jun. 19, 2000, now abandoned, which is a continuation-in-part of application No. 09/250,280, filed on Feb. 16, 1999, now abandoned, which is a continuation-in-part of application No. 09/105,812, filed on Jun. 26, 1998, now abandoned.

(30) Foreign Application Priority Data

Feb. 14, 2000 (WO) .................. PCT/US00/03494

(51) Int. Cl.
*C07H 21/04* (2006.01)
*C12N 9/20* (2006.01)
(52) U.S. Cl. ..................... 435/198; 530/370
(58) Field of Classification Search .............. None
See application file for complete search history.

(56) References Cited

OTHER PUBLICATIONS (Bevan et al., NCBI, GenBank, Accession No. AL021710, Published Feb. 3, 1998).*

* cited by examiner

*Primary Examiner*—Ashwin Mehta
*Assistant Examiner*—Vinod Kumar
(74) *Attorney, Agent, or Firm*—Kenyon & Kenyon LLP

(57) ABSTRACT

Regulation of expression of senescence in plants is achieved by integration of a gene or gene fragment encoding senescence-induced lipase into the plant genome in antisense orientation. The carnation and *Arabidopsis* genes encoding senescence-induced lipase are identified and the nucleotide sequences are used to modify senescence in transgenic plants.

2 Claims, 25 Drawing Sheets

MAEAQPLGLGLSKPGPTWPELLGSNAWAGLLNPLNDE
LRELLRCGDFCQVTYDTFINDQNSSYCGSSRYGKA
DLLHKTAFPGGADRFDVVAYLYATAKVSVPEAFLLK
SRSREKWDRESNWIGYVVVSNDETSRVAGRREVYVV
WRGTCRDYEWVDVLGAQLESAHPLLRTQQTTHVEKV
ENEEKKSIHKSSWYDCFNINLLGSASKDKGSDDD
DDDPKVMQGWMTIYTSEDPKSPFTKLSARTQLQTK
LKQLMTKYKDETLSITFAGHSLGATLSVSAFDIVE
NLTEIPVTAVVFGCPKVGNKFQQLFDSYPNLNVL
HVRNVIDLIPLYPVKLMGYVNIGIELEIDSRKSTFL
KDSKNPSDWHNLQAILHVVSGWHGVKGEFKVVNKRS
VALVNKSCDFLKEECLVPPAWWVVQNKGMVLNKDGE
WVLAPPEEDPTPEFD

FIG.1

```
       1                                                             50
carlip ......MAAE AQPLGLSKPG PTWPELLGSN AWAGLLNPLN DELRELLLRC
arlipl MKRKKKEEEE EKLIVTREFA KRWRDLSGQN HWKGMLQPLD QDLREYIIHY
ipolip .......... .....MSGIA KRWKVLSGSD NWEGLLEPLD SDLRRYLIHY
arlipi MTAEDIRRRD KKTEEERRLR DTWRKIQGED DWAGLMDPMD PILRSELIRY 51                                                            100
carlip GDFCQVTYDT FINDQNSSYC GSSRYGKADL LHKTAFPGGA D..RFDVVAY
arlipl GEMAQAGYDT FNINTESQFA GASIYSRKDF FAKVGLEIAH PYTKYKVTKF
ipolip GTMVSPATDS FINEAASKNV GLPRYARRNL LANCGLVKGN PF.KYEVTKY
arlipi GEMACACYDA FDFDPASKYC GTSRFTRLEF FDSLGMIDSG ....YEVARY 101                                                           150
carlip LYATAKVSVP .EAFLLKSRS REKWDRESNW IGYVVVSNDE TSRVA.GRRE
arlipl IYATSDIHVP .ESFLLFPIS REGWSKESNW MGYVAVTDDQ .GTALLGRRD
ipolip FYAPSTIPLP DEGYNVRATR ADAVLKESNW NGYVAVATDE .GKVALGRRD
arlipi LYATSNINLP ..NFFSKSRW SKVWSKNANW MGYVAVSDDE TSRNRLGRRD 151                                                           200
carlip VYVVWRGTCR DYEWVDVLGA QLESAHPLLR TQQTTHVEKV ENEEKKSIHK
arlipl IVVSWRGSVQ PLEWVEDFEF GLVNAI.... .......... ..........
ipolip ILIVWRGTIR KSEWNENLTF WFVKAP.... .......... ..........
arlipi IAIAWRGTVT KLEWIADLKD YLKPVT.... .......... ..........

201                                                           250
carlip SSWYDCFNIN LLGSASKDKG KGSDDDDDDD PKVMQGWMTI YTSEDPKSPF
arlipl .......... .......... KIFGERNDQ. VQIHQGWYSI YMSQDERSPF
ipolip .......... .......... LFFGQNSDP. L.VHKGWYDM YTTINQDSQL
arlipi .......... .......... ENKIRCPDPA VKVESGFLDL YTDKDTTCKF 251                                                           300
carlip TKLSARTQLQ TKLKQLMTKY KDET...LSI TFAGHSLGAT LSVVSAFDIV
arlipl TKTNARDQVL REVGRLLEKY KDEE...VSI TICGHSLGAA LATLSAIDIV
ipolip NEKSARDQIR EEVARLVELY KDED...ISI TVTGHSLGSS MATLNAVDLA
arlipi ARFSAREQIL TEVKRLVEEH GDDDDSDLSI TVTGHSLGGA LAILSAYDIA
```

FIG.2A

```
       301                                                              350
carlip ENLTTE.... ....IPVTAV VFGCPKVGNK KFQQLFDSYP NLNVLHVRNV
arlipl ANGYNRPKSR PDKSCPVTAF VFASPRVGDS DFRKLFSGLE DIRVLRTRNL
ipolip ANPINN.... .NKNILVTAF LYASPKVGDE NFKNVISNQQ NLRALRISDV
arlipi EMRLNR..SK KGKVIPVTVL TYGGPRVGNV RFRERMEEL. GVKVMRVVNV 351                                                              400
carlip IDLIPLYPVK LMG....... .......... YVNIGIELEI DSRKSTFLKD
arlipl PDVIPIYPPI G......... .......... YSEVGDEFPI DTRKSPYMKS
ipolip NDIVTAVPPF GWKEGDNTAI L......... YGDVGVGLVI DSKKSHYLKP
arlipi HDVVPKSPGL FLNESRPHAL MKIAEGLPWC YSHVGEELAL DHQNSPFLKP 401                                                              450
carlip SKNPSDWHNL QAILHVVSGW HGV.KGE.FK VVNKRSVALV NKSCDFLKEE
arlipl PGNLATFHCL EGYLHGVAGT QGTNKADLFR LDVERAIGLV NKSVDGLKDE
ipolip DFPNLSTHDL MLYMHAIDGY QCSQGG..FE RQEDFDLAKV NKYGDYLKAE
arlipi SVDVSTAHNL EAMLHLLDGY HG..KGERFV LSSGRDHALV NKASDFLKEH 451                                                              500
carlip CLVPPAWWVV QNKGMVLNKD GEWVLAPP.. .EEDPTPEFD ..........
arlipl CMVPGKWRVL KNKGMAQQDD GSWELVDH.E IDDNEDLDF. ..........
ipolip YPIPIGWFNI KDKGMVQQDD GNYILDDH.E VDKTF..... ..........
arlipi LQIPPFWRQD ANKGMVRNSE GRWIQAERLR FEDHHSPDIH HHLSQLRLDH 501
carlip ..
arlipl ..
ipolip
arlipi PC
```

FIG.2B

GCACGAGCCATTCCAAAACTCCTTACACCACTCAAAACTATTCCAACATGGCTGCAGAAGCCCAACCTTTAGGCCTCTC
AAAGCCCGGCCCAACATGGCCCGAACTCCTCGGGTCCAACGCTTGGGCCGGGCTACTAAACCCGCTCAACGATGAGCTC
CGTGAGCTCCTCCTACGCTGCGGGGACTTCTGCCAGGTGACATACGACACCTTCATAAACGACCAGAACTCGTCCTACT
GCGGGCAGCAGCGGCTACGGGAAGGCGGACTACTTCATAAGACCGCGTTTCCCGGGGGCGCAGGTCCGGTTTGACGTGGT
GGCGTACTTGTACGCCACTGCGAAGGTCAGCGTCCCAgAGGCGTTTCTGCTGAAGTCGAGGTCGAGGGAGAAGTGTAA
AGGGAATGGAATTGGATTGTGTCGTGGTATGTCGTGTGTCGAATGACGAGACGAGTCGGGTGGCGGGACGAAgGGAGGTGTATG
TGGTGTGGAGAGGGACTTGTAgGGATTATGAGTGGGTTGATGTTCTTGGTGCTCAACTTGAGTCTGCTCATCCTTTGTT
ACGCACTCAACAAACTACTACTAgTTGAAAAGGTGGAAAAATGAGGAAAAGAAGAGCATTCATAAATCAAGTTGGTACGAC
TGTTTCAATATCAACCTACTAgGTTCCGCGTCCAAAGACAAAGGAAAAGGAAGACGACGACGATGACGACGACCCCA
AAGTGATGCAAGGTTGGATGACAATATACACATCGGAGGATCCCAAATCACCCTTCACAAACTAAGTGCAAGAACACA
ACTTCAGACCAAACTCAAACAACTACTGACAAAATACAAAGACGAAACCCTAAGCATAACATTCGCCGGTCACAGCCTA
GGGCGACACTATCAGTCGTAGGCAACAAAAATTCCAACAACTCTTCGACTCGTACCAACTAAATGTCCTCCATGTAAG
TCGGGTGCCCAAAAGTAGGCAACAAAAATTCCAACAACTCTTCGACTCGTACCAACTAAATGTCCTCCATGTAAG
GAATGTCATCGACCTTGATCCCTCTGTATCCGGTGAAAACTCATGGGTTACGTGAACATAGGAATCGAGCTGGAGATCGAC
TCGAGGAAGTCGACCTTTCTAAAGGACTCGAAAAACCCGAGTGATTTGTAAATAATTTGCAAGCAATATTGCATGTGTAA
GTGGTTGGCATGGGAATGTTTGGTTCCTCCAGCTTGGTGGGTTGTGCAGAACAAAGGGATGGTTTTGAATAAGGATGGTGAG
TCTTAAGGAAGAATGTTTGGTTCCTCCAGCTTGGTGGGTTGTGCAGAACAAAGGGATGGTTTTGAATAAGGATGGTGAG
TGGGTTTGGCTCCTCCTGAGGAAGATCCTACTACTCCTGAATTTATGGGACTAAGTTACTATTTATTGTTTATTATATGTTTATTATATTTGAAATGTGTTTAAG
ATTTACTAAATTTACATGACAATTTATGGGACTAAGTTACTATTTATTGTTTATTATATGTTTATTATATTTGAAATGTGTTTAAG
TTACATAAAATTGCAATTAGTTTTAAAAAAAAAA

——— uncoding region of cDNA clone

FIG.7

Met Ala Ala Glu Ala Gln Pro Leu Gly Leu Ser Lys Pro Gly Pro Thr Trp Pro Glu Leu
 1                   5                  10                  15                  20

Leu Gly Ser Asn Ala Trp Ala Gly Leu Leu Asn Pro Leu Asn Asp Glu Leu Arg Glu Leu
 21                  25                  30                  35                  40

Leu Leu Arg Cys Gly Asp Phe Cys Gln Val Thr Tyr Asp Thr Phe Ile Asn Asp Gln Asn
 41                  45                  50                  55                  60

Ser Ser Tyr Cys Gly Ser Ser Arg Tyr Gly Lys Ala Asp Leu Leu His Lys Thr Ala Phe
 61                  65                  70                  75                  80

Pro Gly Ala Asp Arg Phe Asp Val Val Ala Tyr Leu Tyr Ala Thr Ala Lys Val Ser
 81                  85                  90                  95                  100

Val Pro Glu Ala Phe Leu Leu Lys Ser Arg Ser Arg Glu Lys Trp Asp Arg Glu Ser Asn
 101                 105                 110                 115                 120

Trp Ile Gly Tyr Val Val Val Ser Asn Asp Glu Thr Ser Arg Val Ala Gly Arg Arg Glu
 121                 125                 130                 135                 140

Val Tyr Val Val Trp Arg Gly Thr Cys Arg Asp Tyr Glu Trp Val Asp Val Leu Gly Ala
 141                 145                 150                 155                 160

Gln Leu Glu Ser Ala His Pro Leu Leu Arg Thr Gln Gln Thr His Val Glu Lys Val
 161                 165                 170                 175                 180

Glu Asn Glu Glu Lys Lys Ser Ile His Lys Ser Ser Trp Tyr Asp Cys Phe Asn Ile Asn
 181                 185                 190                 195                 200

Leu Leu Gly Ser Ala Ser Lys Asp Lys Gly Lys Gly Leu Lys Gly Ser Asp Asp Asp Asp
 201                 205                 210                 215                 220

FIG.8A

| Pro 221 | Lys | Val | Met | Gln | Gly | Trp | Met | Thr | Ile 230 | Tyr | Thr | Ser | Glu | Asp 235 | Pro | Lys | Ser | Pro | Phe 240 |
|---|---|---|---|---|---|---|---|---|---|---|---|---|---|---|---|---|---|---|---|
| Thr 241 | Lys | Leu | Ser | Ala | Arg | Thr | Gln | Leu | Gln 250 | Thr | Lys | Leu | Lys | Gln 255 | Leu | Met | Thr | Lys | Tyr 260 |
| Lys 261 | Asp | Glu | Thr | Leu | Ser | Ile | Thr | Phe | Ala 270 | Gly | His | Ser | Leu | Gly 275 | Ala | Thr | Leu | Ser | Val 280 |
| Val 281 | Ser | Ala | Phe | Asp | Ile | Val | Glu | Asn | Leu 290 | Thr | Thr | Glu | Ile | Pro 295 | Val | Thr | Ala | Val | Val 300 |
| Phe 301 | Gly | Cys | Pro | Lys | Val | Gly | Asn | Lys | Lys 310 | Phe | Gln | Gln | Leu | Phe 315 | Asp | Ser | Tyr | Pro | Asn 320 |
| Leu 321 | Asn | Val | Leu | His | Val | Arg | Asn | Val | Ile 330 | Asp | Leu | Ile | Pro | Leu 335 | Tyr | Pro | Val | Lys | Leu 340 |
| Met 341 | Gly | Tyr | Val | Asn | Ile | Gly | Ile | Leu | Glu 350 | Leu | Glu | Ile | Asp | Ser 355 | Arg | Lys | Ser | Thr | Phe 360 |
| Lys 361 | Asp | Ser | Lys | Asn | Pro | Ser | Asp | Trp | His 370 | Asn | Leu | Gln | Ala | Ile 375 | Leu | His | Val | Val | Ser 380 |
| Gly 381 | Trp | His | Gly | Val | Lys | Gly | Glu | Phe | Lys 390 | Val | Val | Asn | Lys | Ser 395 | Val | Ala | Leu | Val 400 |
| Asn 401 | Lys | Ser | Cys | Asp | Phe | Leu | Lys | Glu | Cys 410 | Leu | Val | Pro | Pro 415 | Ala | Trp | Trp | Val 420 |
| Gln 421 | Asn | Lys | Gly | Met | Val | Leu | Asn | Lys | Asp 430 | Gly | Glu | Trp | Val | Leu 435 | Ala | Pro | Pro | Glu | Glu 440 |
| Asp 441 | Pro | Thr | Pro | Glu | Phe | Asp |

```
1/1                                   31/11
CGG GTC GAC CCA CGC GTC CGC GAA AAC GCT TCC GAC TAC GAg GTT GTA AAC TTC CTC TAC GCC ACA GCT CGT GTT TCT CTC CCC GAA GGT
 R   V   D   P   R   V   R   E   N   A   S   D   Y   E   V   V   N   F   L   Y   A   T   A   R   V   S   L   P   E   G
91/31                                                    61/21
TTG CTT CTC CAA TCA AGA gAT TCT TGG GAC CGT GAG TCT AAC TGG TTT GGC TAC ATT GCT GTC ACG TCT GAT GAA CGG TCT AAG
 L   L   L   Q   S   R   D   S   W   D   R   E   S   N   W   F   G   Y   I   A   V   T   S   D   E   R   S   K
181/61                                                   151/51
GCT TTA GGA CGC GTC GAG ATC TAT ATA GCT AGA ACG AGC AGG AAC TAT GAG TGG GTC AAT GTT TTG GGT GCT AGG CCA ACT TCA
 A   L   G   R   V   E   I   Y   I   A   R   T   S   R   N   Y   E   W   V   N   V   L   G   A   R   P   T   S
271/91                                                   241/81
GCT GAC CCC TTG CTG CAC GGA CCC GAG CAG GAT GGT GTA GTT GAA GGT ACG ACT TTT GAT AGT GAC AGT CTA CGG TCA CAG TTG
 A   D   P   L   L   H   G   P   E   Q   D   G   V   V   E   G   T   T   F   D   S   D   S   L   R   S   Q   L
361/121                                                  331/111
GGG TGT AAG GTG ATG CTC GGG TGG CTC ACA ATC TAT ACT TCT AAT CAC CCC GAA TCG AAA CTG ACT AAG CTG ACT TTC ACT
 G   C   K   V   M   L   G   W   L   T   I   Y   T   S   N   H   P   E   S   K   L   T   K   L   T   F   T
451/151                                                  421/141
TTA GCC AAG ATC AAG GAG CTT CTG TTG AAG TAT AAG GAC GAG AAA CCG AGC ATT GTG TTG ACT GGA CAT AGC TTG GGA CCT ACA GAG GCT
 L   A   K   I   K   E   L   L   L   K   Y   K   D   E   K   P   S   I   V   L   T   G   H   S   L   G   A   T   E   A
541/181                                                  511/171
GTT CTG GCC GCC TAT GAT GAG AAC GGT TCC AGT GAC GAT ATA GTC ACT GCT ATA GTC TTT GGT TGT CCA CAG GTA GGA AAC
 V   L   A   A   Y   D   E   N   G   S   S   D   D   I   V   T   A   I   V   F   G   C   P   Q   V   G   N
631/211                                                  601/201
AAG GAG TTC AGA GAC GAA GTA ATG AGT CAC AAG AAC TTA AAG ATC CTC CAT GTA AGG AAC ACG ATT GAT CTC TTA ACT CGA TAC CCA GGG
 K   E   F   R   D   E   V   M   S   H   K   N   L   K   I   L   H   V   R   N   T   I   D   L   L   T   R   Y   P   G
                                                         691/231
```

FIG. 13A

```
721/241                                               751/251
GGA CTT TTA GGG TAT GTG GAC ATA GGa ATA AAC TTT GTG ATC GAT ACA AAG AAG TCA AGG AAT CCA GGG GAT
 G   L   L   G   Y   V   D   I   G   I   N   F   V   I   D   T   K   K   S   R   N   P   G   D
811/271                                               781/261
TGG CAT AAT cTT CAG GCG ATG TTA CAT GTT AAA CTG ATG GTT AAG AGA AGT ATT GCA
 W   H   N   L   Q   A   M   L   H   V   K   L   M   V   K   R   S   I   A
                                                      871/291
                                TTC CTA AGC GAT TCA AGG
                                 F   L   S   D   S   R
                                841/281
                GTA GCT GGA TGG AAT GGG GAG TTT AAA CTG ATG GTT AAG AGA AGT ATT GCA
                 V   A   G   W   N   G   E   F   K   L   M   V   K   R   S   I   A
901/301                                               961/321
TTA GTG AAC AAG TCA TGC GAG TTc TTG AAA GCT GAG TGT TTG GTG CCA GGA TCT TGG TGG GTA GAG AAG AAC AAA GGA CTG ATC AAG AAC
 L   V   N   K   S   C   E   F   L   K   A   E   C   L   V   P   G   S   W   W   V   E   K   N   K   G   L   I   K   N
991/331                                              1051
GAA GAT GGT GAA TGG GTT cTT GCT CCC GTT GAA GAA GAA CCT GTA CCT GAA TTC TAA ATT GTA TTT CTG TAT TTT TCT CTA AGG TCA TGA
 E   D   G   E   W   V   L   A   P   V   E   E   E   P   V   P   E   F   *
                                1021/341
1081
TAA ATC AAC AAT AAG CAG TTC AAC TAT GTG ATG AAA AGA CCC AAG TTA TTA TAT TGA TAT GAG TTT ATG AGA TAA AAA AAA AAA
1141                                                  1165
                                                      AAA

Note: The identity of nucleotides indicated in lower case needs to be
confirmed.
```

FIG.13B

Sequence of *Aradopsis thaliana* senescence lipase

```
ATGACGGCGGAAGATATTCGCCGGCGAGATAAAAAAACCGAAGAAGAAAGAAGACTAAGAG
 M  T  A  E  D  I  R  R  R  D  K  K  T  E  E  E  R  R  L  R
ACACGTGGCGTAAGATCCAAGGAGAAGACGATTGGGCCGGGTTAATGGATCCAATGGATCCA
 D  T  W  R  K  I  Q  G  E  D  D  W  A  G  L  M  D  P  M  D  P
ATTCTTAGATCGGAGCTAATCCGTTACGGCGAAATGGCTCAAGCTTGTTACGACGCTTTCGAT
 I  L  R  S  E  L  I  R  Y  G  E  M  A  Q  A  C  Y  D  A  F  D
TTCGATCCCGCTTCCAAATACTGCGGCACCTCCAGGTTCACGCGACTCGAGTTCTTCGATTCTC
 F  D  P  A  S  K  Y  C  G  T  S  R  F  T  R  L  E  F  F  D  S
TCGGAATGATCGATTCCGGTTACGAGGTGGCGCGTTACCTCTACGCGACGTCGAACATCAATC
 L  G  M  I  D  S  G  Y  E  V  A  R  Y  L  Y  A  T  S  N  I  N
TCCCGAACTTCTTCTCGAAATCGCGGTGGTCTAAAGTCTGGAGCAAAAACGCTAATTGGATGG
 L  P  N  F  F  S  K  S  R  W  S  K  V  W  S  K  N  A  N  W  M
GATACGTCGCCGTTTCAGACGACGAAACGTCTCGTAACCGACTCGGCCGCCGTGATATCGCGA
 G  Y  V  A  V  S  D  D  E  T  S  R  N  R  L  G  R  R  D  I  A
TTGCGTGGAGAGGAACCGTTACGAAACTTGAATGGATCGCGGATCTAAAGGATTATTTAAAA
 I  A  W  R  G  T  V  T  K  L  E  W  I  A  D  L  K  D  Y  L  K
CCGGTAACCGAAAACAAGATCCGATGCCCCGACCCGGCCGTTAAAGTCGAATCCGGATTCTTA
 P  V  T  E  N  K  I  R  C  P  D  P  A  V  K  V  E  S  G  F  L
GATCTCTACACTGACAAAGACACAACCTGCAAATTCGCGAGATTCTCAGCGCGTGAACAGATT
 D  L  Y  T  D  K  D  T  T  C  K  F  A  R  F  S  A  R  E  Q  I
TTAACGGAGGTGAAACGGTTAGTGGAAGAACACGGCGACGACGATGATTCCGATTTAAGCAT
 L  T  E  V  K  R  L  V  E  E  H  G  D  D  D  D  S  D  L  S
CACCGTGACGGGACACAGTCTCGGCGGCGCGTTAGCGATATTAAGCGCGTACGATATAGCGG
                                       A  L  A  I  L  S  A  Y  D  I  A
AGATGAGATTGAATCGGAGTAAGAAAGGGAAAGTGATTCCGGTGACGGTGTTGACATACGGA
 E  M  R  L  N  R  S  K  K  G  K  V  I  P  V  T  V  L  T  Y  G
GGACCGAGAGTTGGGAACGTTAGGTTTAGGGAGAGGATGGAGGAATTGGGAGTGAAAGTGAT
 G  P  R  V  G  N  V  R  F  R  E  R  M  E  E  L  G  V  K  V  M
GAGAGTAGTGAATGTTCACGACGTGGTTCCCAAGTCGCCGGGATTGTTTTTGAACGAGAGTAG
 R  V  V  N  V  H  D  V  V  P  K  S  P  G  L  F  L  N  E  S  R
ACCTCACGCGCTGATGAAGATAGCGGAGGGGTTGCCGTGGTGTTATAGCCACGTGGGGGAGG
 P  H  A  L  M  K  I  A  E  G  L  P  W  C  Y  S  H  V  G  E
AGCTGGCGTTGGATCATCAGAACTCGCCGTTTCTTAAACCTTCCGTTGATGTTTCTACTGCTCA
 E  L  A  L  D  H  Q  N  S  P  F  L  K  P  S  V  D  V  S  T  A  H
TAATCTTGAAGCTATGCTTCATTTACTTGACGGGTATCATGGAAAAGGAGAGAGATTTGTGCT
 N  L  E  A  M  L  H  L  L  D  G  Y  H  G  K  G  E  R  F  V  L
GTCGAGTGGGAGAGACCATGCGCTAGTGAACAAAGCGTCGGACTTTTTGAAAGAGCATTTAC
 S  S  G  R  D  H  A  L  V  N  K  A  S  D  F  L  K  E  H  L
AAATTCCACCGTTTTGGCGTCAAGACGCGAATAAAGGAATGGTTCGGAACAGTGAAGGTCGT
 Q  I  P  P  F  W  R  Q  D  A  N  K  G  M  V  R  N  S  E  G  R
TGGATTCAAGCCGAGCGTCTCCGTTTTGAGGATCATCATTCTCCTGATATCCACCACCATCTCT
 W  I  Q  A  E  R  L  R  F  E  D  H  H  S  P  D  I  H  H  H  L
CTCAGCTCCGTCTTGATCATCCTTGTTAA
 S  Q  L  R  L  D  H  P  C
```

FIG.14

Northern Blot of Ethephon-treated
*Arabidopsis thaliana* Leaf Tissue
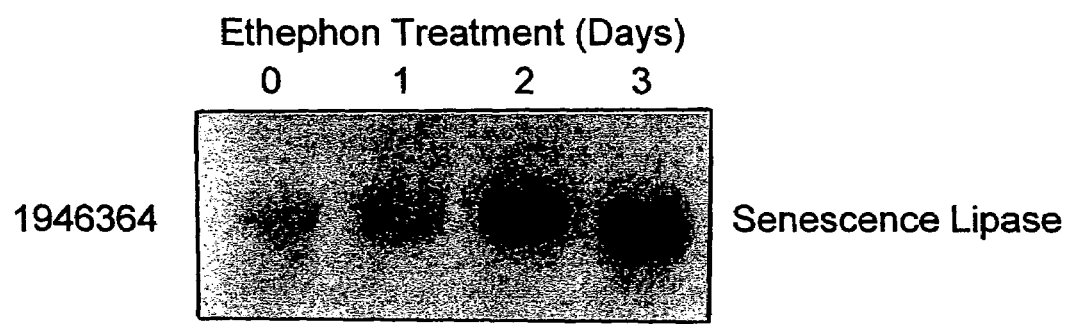
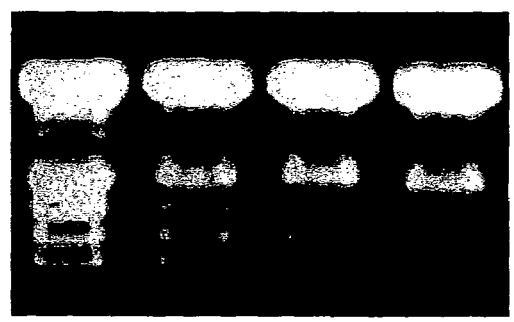
FIG.16

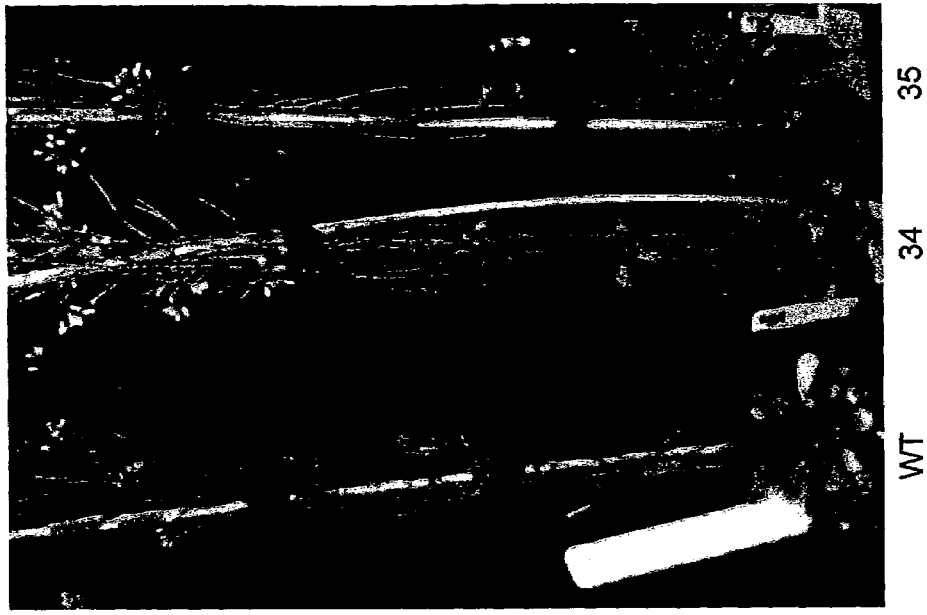
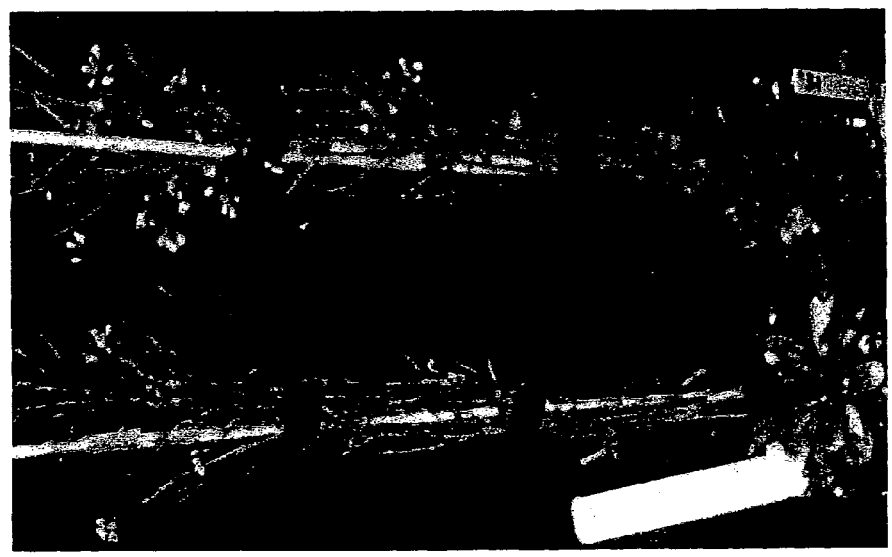
FIG. 18

US 7,087,419 B2

DNA ENCODING A PLANT LIPASE, TRANSGENIC PLANTS AND A METHOD FOR CONTROLLING SENESCENCE IN PLANTS

This application is a continuation of application Ser. No. 09/610,104, filed on Jul. 5, 2000 (now U.S. Pat. No. 6,774, 284), which is a continuation-in-part of application of application Ser. No. 09/597,774, filed Jun. 19, 2000 (Abandoned), which is a continuation-in-part of application of application Ser. No. 09/250,280, filed Feb. 16, 1999 (Abandoned), which is a continuation-in-part application of application Ser. No. 09/105,812, filed Jun. 26, 1998 (Abandoned), and incorporated herein in its entirety by reference thereto.

FIELD OF THE INVENTION

The present invention relates to polynucleotides which encode plant polypeptides and which exhibit senescence-induced expression, transgenic plants containing the polynucleotides in antisense orientation and methods for controlling senescence in plants. More particularly, the present invention relates to plant lipase genes whose expression is induced by the onset of senescence and the use of the lipase gene to control senescence in plants.

DESCRIPTION OF THE PRIOR ART

Senescence is the terminal phase of biological development in the life of a plant. It presages death and occurs at various levels of biological organization including the whole plant, organs, flowers and fruit, tissues and individual cells.

Cell membrane deterioration is an early and fundamental feature of senescence. Metabolism of lipids, in particular membrane lipids, is one of several biochemical manifestations of cellular senescence. Rose petals, for example, sustain an increase in acyl hydrolase activity as senescence progresses that is accompanied by a loss of membrane function (Borochov, et al., Plant Physiol., 1982, 69, 296–299). Cell membrane deterioration is an early and characteristic feature of senescence engendering increased permeability, loss of ionic gradients and decreased function of key membrane proteins such as ion pumps (Brown, et al., Plant Physiol.: A Treatise, Vol. X. Academic Press, 1991, pp.227–275). Much of this decline in membrane structural and functional integrity can be attributed to lipase-mediated phospholipid metabolism. Loss of lipid phosphate has been demonstrated for senescing flower petals, leaves, cotyledons and ripening fruit (Thompson, J. E., Senescence and Aging in Plants, Academic Press, San Diego, 1988, pp. 51–83), and this appears to give rise to major alterations in the molecular organization of the membrane bilayer with advancing senescence that lead to impairment of cell function. In particular, studies with a number of senescing plant tissues have provided evidence for lipid phase separations in membranes that appear to be attributable to an accumulation of lipid metabolites in the membrane bilayer (McKersie and Thompson, 1979, Biochim. Biophys. Acta, 508: 197–212; Chia, et al., 1981, Plant Physiol., 67:415–420). There is growing evidence that much of the metabolism of lipids in senescing tissue is achieved through senescence-specific changes in gene expression (Buchanan-Wollaston, V., J. Exp. Bot., 1997, 307:181–199).

The onset of senescence can be induced by different factors both internal and external. For example, ethylene plays a role in many plants in a variety of plant processes such as seed germination, seedling development, fruit ripening and flower senescence. Ethylene production in plants can also be associated with trauma induced by mechanical wounding, chemicals, stress (such as produced by temperature and water amount variations), and by disease. Ethylene has been implicated in the regulation of leaf senescence in many plants, but evidence obtained with transgenic plants and ethylene response mutants has indicated that, although ethylene has an effect on senescence, it is not an essential regulator of the process. In many plants ethylene seems to have no role in fruit ripening or senescence. For example in the ripening of fruits of non-climacteric plants such as strawberry, in senescence of some flowers such as day lilies and in leaf senescence in some plants, such as *Arabidopsis*, and in particular, in the monocots there is no requirement for ethylene signaling (Smart, C. M., 1994, New Phytology, 126:419–448; Valpuesta, et al., 1995, Plant Mol. Biol., 28:575–582).

External factors that induce premature initiation of senescence include environmental stresses such as temperature, drought, poor light or nutrient supply, as well as pathogen attack. As in the case of natural (age-related) senescence, environmental stress-induced senescence is characterized by a loss of cellular membrane integrity. Specifically, exposure to environmental stress induces electrolyte leakage reflecting membrane damage (Sharom, et al., 1994, Plant Physiol., 105:305–308; Wright and Simon, 1973, J. Exp. Botany, 24:400–411; Wright, M., 1974, Planta,120:63–69; and Eze et al., 1986, Physiologia Plantarum, 68:323–328), a decline in membrane phospholipid levels (Wright, M., 1974, Planta, 120:63–69) and lipid phase transitions (Sharom, et al., 1994, Plant Physiol., 105:305–308), all of which can be attributed to the action of lipase. Plant tissues exposed to environmental stress also produce ethylene, commonly known as stress ethylene (Buchanan-Wollaston, V., 1997, J. Exp. Botany, 48:181–199; Wright, M., 1974, Planta,120:63–69). As noted above, ethylene is known to cause senescence in some plants.

Membrane deterioration leading to leakage is also a seminal feature of seed aging, and there is evidence that this too reflects deesterification of fatty acids from membrane phospholipids (McKersie, B. D., Senarata, T., Walker, M. A., Kendall, E. J. and Hetherington, P. R. In: Senescence and Aging in Plants, Ed. L. D. Nooden and A. C. Leoopold, academic Press, 1988. PP 441–464).

Presently, there is no widely applicable method for controlling onset of senescence caused by either internal or external, e.g., environmental stress, factors. At present, the technology for controlling senescence and increasing the shelf-life of fresh, perishable plant produce, such as fruits, flowers and vegetables relies primarily upon reducing ethylene biosynthesis. For example, U.S. Pat. No. 5,824,875 discloses transgenic geranium plants which exhibit prolonged shelf-life due to reduction in levels of ethylene resulting from the expression of one of three 1-aminocyclopropane-1-carboxylate (ACC) synthase genes in antisense orientation. Consequently, this technology is applicable to only a limited range of plants that are ethylene-sensitive.

The shelf-life of some fruits is also extended by reducing ethylene biosynthesis, which causes ripening to occur more slowly. Since senescence of these fruits is induced after ripening, the effect of reduced ethylene biosynthesis on shelf-life is indirect. Another approach used to delay fruit ripening is by altering cellular levels of polygalacturonase, a cell-wall softening enzyme that is synthesized during the early stages of ripening. This approach is similar to controlling ethylene biosynthesis in that it, too, only indirectly affects senescence and again, is only applicable to a narrow range of plants.

Thus, there is a need for a method of controlling senescence in plants which is applicable to a wide variety of plants. It is therefore of interest to develop senescence modulating technologies that are applicable to all types of plants, regardless of ethylene sensitivity.

SUMMARY OF THE INVENTION

This invention is based on the discovery and cloning of a full length cDNA clone encoding a carnation senescence-induced lipase and a full-length cDNA clone encoding *Arabidopsis thaliana* senescence-induced lipase. The nucleotide sequences and corresponding amino acid sequences for the senescence-induced lipase genes are disclosed herein. The nucleotide sequence of the carnation senescence-induced lipase gene has been successfully used as a heterologous probe to detect corresponding genes or RNA transcripts in several plants that are similarly regulated.

The invention provides a method for genetic modification of plants to control the onset of senescence, either age-related senescence or environmental stress-induced senescence. The senescence-induced lipase nucleotide sequences of the invention, fragments thereof, or combinations of such fragments, are introduced into a plant cell in reverse orientation to inhibit expression of the endogenous senescence-induced lipase gene, thereby reducing the level of endogenous senescence-induced lipase and altering senescence in the transformed plant.

Using the methods of the invention, transgenic plants are generated and monitored for growth and development. Plants or detached parts of plants (e.g., cuttings, flowers, vegetables, fruits, seeds or leaves) exhibiting prolonged life or shelf life with respect to plant growth, flowering, reduced fruit spoilage, reduced seed aging and/or reduced yellowing of leaves due to reduction in the level of senescence-induced lipase are selected as desired products having improved properties including reduced leaf yellowing, reduced petal abscission, reduced fruit spoilage during shipping and storage. These superior plants are propagated. Similarly, plants exhibiting increased resistance to environmental stress, e.g., decreased susceptibility to low temperature (chilling), drought, infection, etc., are selected as superior products.

In one aspect, the present invention is directed to an isolated DNA molecule encoding senescence-induced lipase, wherein the DNA molecule hybridizes with SEQ ID NO:1, or a functional derivative of the isolated DNA molecule which hybridizes with SEQ ID NO:1. In one embodiment of the invention, the isolated DNA molecule has the nucleotide sequence of SEQ ID NO:1, i.e., 100% complementarity (sequence identity) to SEQ ID NO:1. In another embodiment of this aspect of the invention, the isolated DNA molecule contains the nucleotide sequence of SEQ ID NO:4.

The invention is also directed to an isolated DNA molecule encoding senescence-induced lipase, wherein the DNA molecule hybridizes with SEQ ID NO:18, or a functional derivative of the isolated DNA molecule which hybridizes with SEQ ID NO:18. In one embodiment of this aspect of the invention, the isolated DNA molecule has the nucleotide sequence of SEQ ID NO:18, i.e., 100% complementarity (sequence identity) to SEQ ID NO:18. In another embodiment of this aspect of the invention, the isolated DNA molecule contains the nucleotide sequence of SEQ ID NO:19.

In another embodiment of the invention, there is provided an isolated protein encoded by a DNA molecule as described herein above, or a functional derivative thereof. A preferred protein has the amino acid sequence of SEQ ID NO:2, or is a functional derivative thereof.

Also provided herein is an antisense oligonucleotide or polynucleotide encoding an RNA molecule which is complementary to at least a portion of an RNA transcript of the DNA molecule described hereinabove, wherein the RNA molecule hybridizes with the RNA transcript such that expression of endogenous senescence-induced lipase is altered. The antisense oligonucleotide or polynucleotide can be full length or preferably has about six to about 100 nucleotides.

The antisense oligonucleotide or polynucleotide is substantially complementary to a corresponding portion of one strand of a DNA molecule encoding senescence-induced lipase, wherein the DNA molecule encoding senescence-induced lipase hybridizes with SEQ ID NO:1, SEQ ID NO:18 or both, or is substantially complementary to a corresponding portion of an RNA sequence encoded by the DNA molecule encoding senescence-induced lipase. In one embodiment of the invention, the antisense oligonucleotide or polynucleotide is substantially complementary to a corresponding portion of one strand of the nucleotide sequence SEQ ID NO:1, SEQ ID NO:18 or both or the RNA transcript encoded by SEQ ID NO:1. In another embodiment, the antisense oligonucleotide is substantially complementary to a corresponding portion of about 100 to about 200 nucleotides of the 5' non-coding portion or 3'-end portion of one strand of a DNA molecule encoding senescence-induced lipase, wherein the DNA molecule hybridizes with SEQ ID NO:1, SEQ ID NO:18 or both. In another embodiment, the antisense oligo- or polynucleotide is substantially complementary to a corresponding portion of the open reading frame of one strand of the nucleotide sequence SEQ ID NO:4 or the RNA transcript encoded by SEQ ID NO:4.

The invention is further directed to a vector for transformation of plant cells, comprising (a) antisense nucleotide sequences substantially complementary to (1) a corresponding portion of one strand of a DNA molecule encoding senescence-induced lipase, wherein the DNA molecule encoding senescence-induced lipase hybridizes with SEQ ID NO:1, SEQ ID NO:18 or both or (2) a corresponding portion of an RNA sequence encoded by the DNA molecule encoding senescence-induced lipase; and (b) regulatory sequences operatively linked to the antisense nucleotide sequences such that the antisense nucleotide sequences are expressed in a plant cell into which it is transformed.

The regulatory sequences include a promoter functional in the transformed plant cell, which promoter may be inducible or constitutive. Optionally, the regulatory sequences include a polyadenylation signal.

The invention also provides a plant cell transformed with the vector as described above, a plantlet or mature plant generated from such a cell, or a plant part of such a plantlet or plant.

The present method is further directed to a method of producing a plant having a reduced level of senescence-induced lipase compared to an unmodified plant, comprising:

(1) transforming a plant with a vector as described above;
(2) allowing the plant to grow to at least a plantlet stage;
(3) assaying the transformed plant or plantlet for altered senescence-induced lipase activity and/or altered senescence and/or altered environmental stress-induced senescence and/or ethylene-induced senescence; and
(4) selecting and growing a plant having altered senescence-induced lipase activity and/or altered senescence and/or altered environmental stressed-induced senescence or ethylene-induced senescence compared to an nom-transformed plant.

A plant produced as above, or progeny, hybrids, clones or plant parts preferably exhibit reduced senescence-induced lipase expression and delayed senescence and/or delayed stress-induced senescence or ethylene-induced senescence.

This invention is further directed to a method of inhibiting expression of endogenous senescence-induced lipase in a plant cell, said method comprising:
(1) integrating into the genome of a plant a vector comprising
  (A) antisense nucleotide sequences complementary to (i) a corresponding portion of one strand of a DNA molecule encoding endogenous senescence-induced lipase, wherein the DNA molecule encoding the endogenous senescence-induced lipase hybridizes with SEQ ID NO:1, SEQ ID NO:18 or both, or (ii) a corresponding portion of an RNA sequence encoded by the endogenous senescence-induced lipase gene; and
  (B) regulatory sequences operatively linked to the antisense nucleotide sequences such that the antisense nucleotide sequences are expressed; and
(2) growing said plant, whereby said antisense nucleotide sequences are transcribed and the transcript binds to said endogenous RNA whereby expression of said senescence-induced lipase gene is inhibited.

BRIEF DESCRIPTION OF THE DRAWINGS

FIG. 1 depicts the derived amino acid sequence (SEQ ID NO:2) encoded by the senescence-induced lipase cDNA clone (SEQ ID NO:1) obtained from a carnation flower cDNA library. Consensus motifs within the amino acid sequence are as follows: single underline, amidation site; dotted underline, protein kinase C phosphorylation site; double underline, N-myristoylation site; box border, cAMP phosphorylation site; shadow box, casein kinase II phosphorylation site; cross-hatched box, consensus sequence of lipase family; and dotted box, N-glycosylation site.

FIG. 2A and FIG. 2B depicts the derived full length carnation petal senescence-induced lipase amino acid sequence (SEQ ID NO:2) in alignment with partial sequences of lipase-like proteins. Carlip, full length sequence of carnation petal senescence-induced lipase (SEQ ID NO:11); arlip, partial sequence of lipase-like protein from *Arabidopsis thaliana* (Gen Bank Accession No. AL021710) (SEQ ID NO:12); ipolip, partial sequence of a lipase-like sequence from *Ipomea* (Gen Bank Accession No. U55867) (SEQ ID NO:13); arlipi, partial sequence of lipase-like protein from *Arabidopsis thaliana* (Gen Bank Accession No. U93215) (SEQ ID NO:14). Identical amino acids among three or four of the sequences are boxed.

FIG. 4 is a Northern blot analysis of RNA isolated from carnation flower petals at different stages of development.

FIG. 7 is the nucleotide sequence of the carnation senescence-induced lipase cDNA clone (SEQ ID NO:1). Solid underlining, non-coding sequence of the senescence-induced lipase cDNA; non-underlined sequenced is the open reading frame.

FIG. 8A and FIG. 8B is the amino acid sequence of the carnation senescence-induced lipase cDNA (SEQ ID NO:2).

FIG. 9A is an ethidium bromide stained gel showing that each of the lanes was loaded with a constant amount of carnation RNA (petals: lanes 1 and 2; leaves: lanes 3 and 4; +, ethylene treated; −, untreated).

FIG. 10 is a partial nucleotide sequence of tomato leaf genomic senescence-induced lipase (SEQ ID NO:6) and the corresponding deduced amino acid sequence (SEQ ID NO:17). The conserved lipase consensus motif is shaded; the sequences of the primers used to generate the genomic fragment are each underlined.

FIG. 13A and FIG. 13B is a partial nucleotide sequence (SEQ ID NO:15) and corresponding deduced amino acid sequence of an *Arabidopsis* EST (GenBank Acc#: N38227)

(SEQ ID NO:16) that is 55.5% identical over a 64 amino acid region with the carnation senescence-induced lipase. The conserved lipase consensus motif is shaded.

FIG. 14 is the nucleotide (top) (SEQ ID No:18) and derived amino acid sequence (bottom) (SEQ ID NO:19) of the full-length *Arabidopsis* senescence-induced lipase gene.

Figure 15:
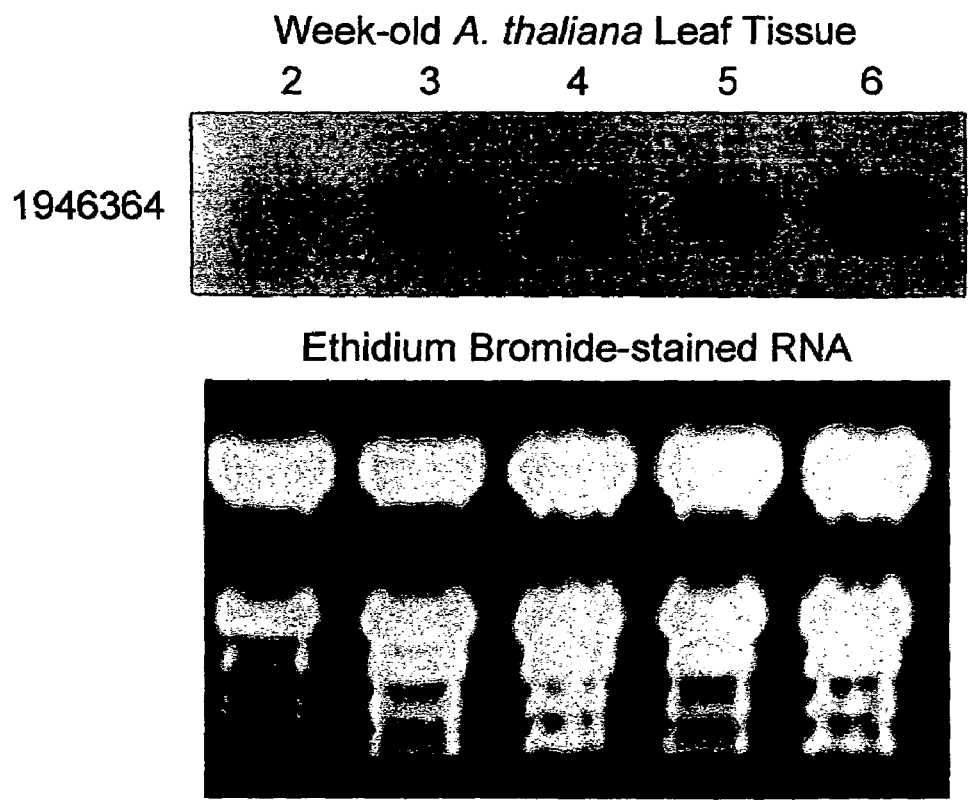

FIG. 15 is a Northern blot of total RNA isolated from leaves of *Arabidopsis* plants at various stages (lane 1, two week-old plants; lane 2, three week-old plants; lane 3, four week-old plants; lane 4, five week-old plants; lane 5, six week-old plants) probed with $^{32}$P-dCTP-labelled full-length *Arabidopsis* senescence-induced lipase. The autoradiograph is at the top Upper Panel and the ethidium bromide stained gel below Lower Panel.

FIG. 16 is a Northern blot of total RNA isolated from leaves of three week-old *Arabidopsis* plants treated with 50 μM ethephon (a source of ethylene) and probed with $^{32}$P-dCTP-labelled full-length *Arabidopsis* senescence-induced lipase. The autoradiograph is at the top Upper Panel and the ethidium bromide stained gel below Lower Panel.

Figure 17:
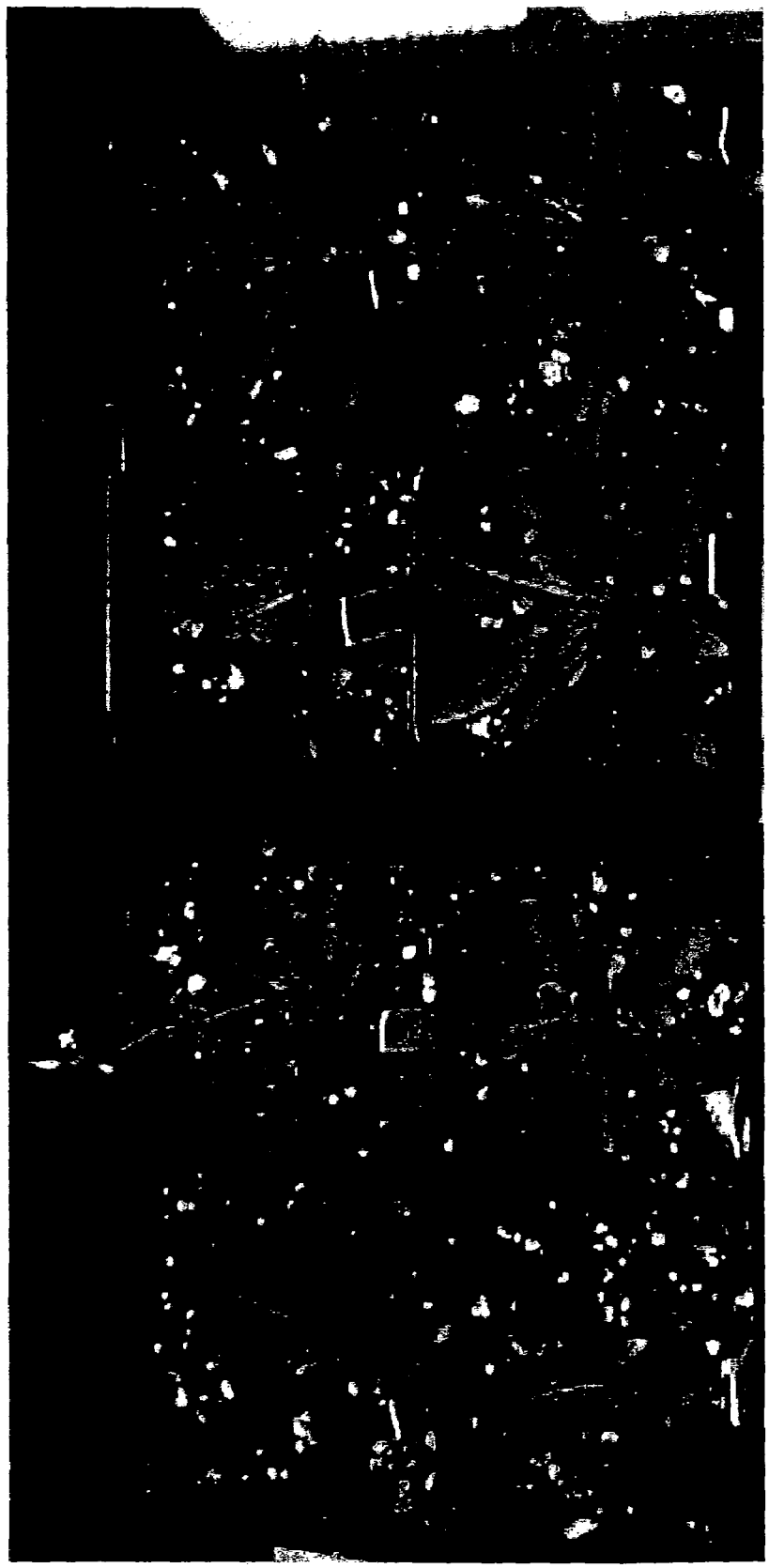

FIG. 17 is a photograph of 4.6 week-old *Arabidopsis* wild-type plants (left) and transgenic plants (right) expressing the full-length *Arabidopsis* senescence-induced lipase gene in antisense orientation showing increased leaf size in the transgenic plants.

FIG. 18 is a photograph of 6.3 week-old *Arabidopsis* wild-type plants (left) and transgenic plants (right) expressing the full-length *Arabidopsis* senescence-induced lipase gene in antisense orientation showing increased leaf size and delayed leaf senescence in the transgenic plants.

Figure 19:

FIG. 19 is a photograph of 7 week-old *Arabidopsis* wild-type plants (left) and transgenic plants (right) expressing the full-length *Arabidopsis* senescence-induced lipase gene in antisense orientation showing increased leaf size in the transgenic plants.

Figure 20:
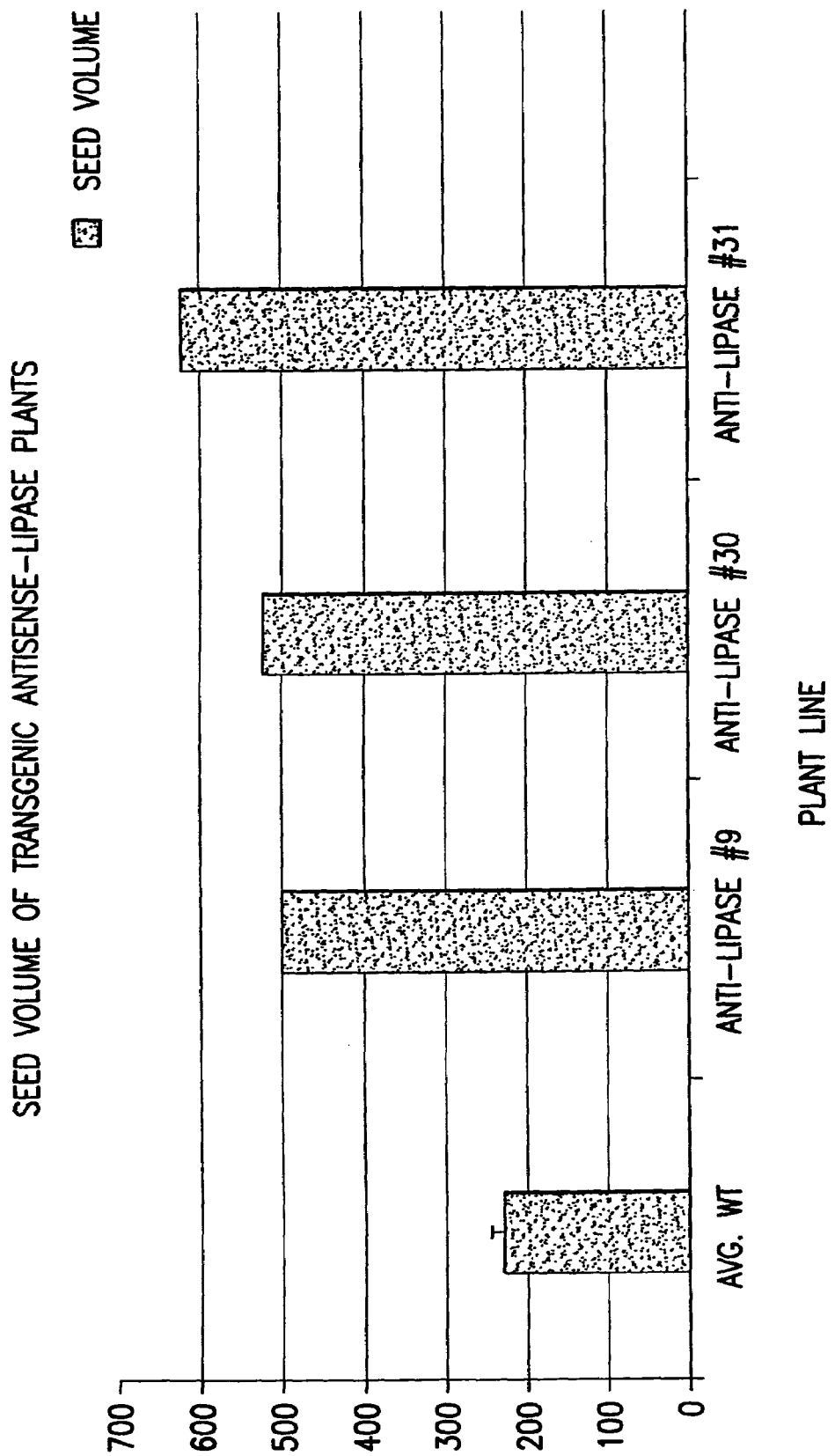

FIG. 20 is a graph showing the increase in seed yield in three $T_1$ transgenic *Arabidopsis* plant lines expressing the senescence-induced lipase gene in antisense orientation. Seed yied is expressed as volume of seed. SE for n=30 is shown for wild-type plants.

Figure 21:
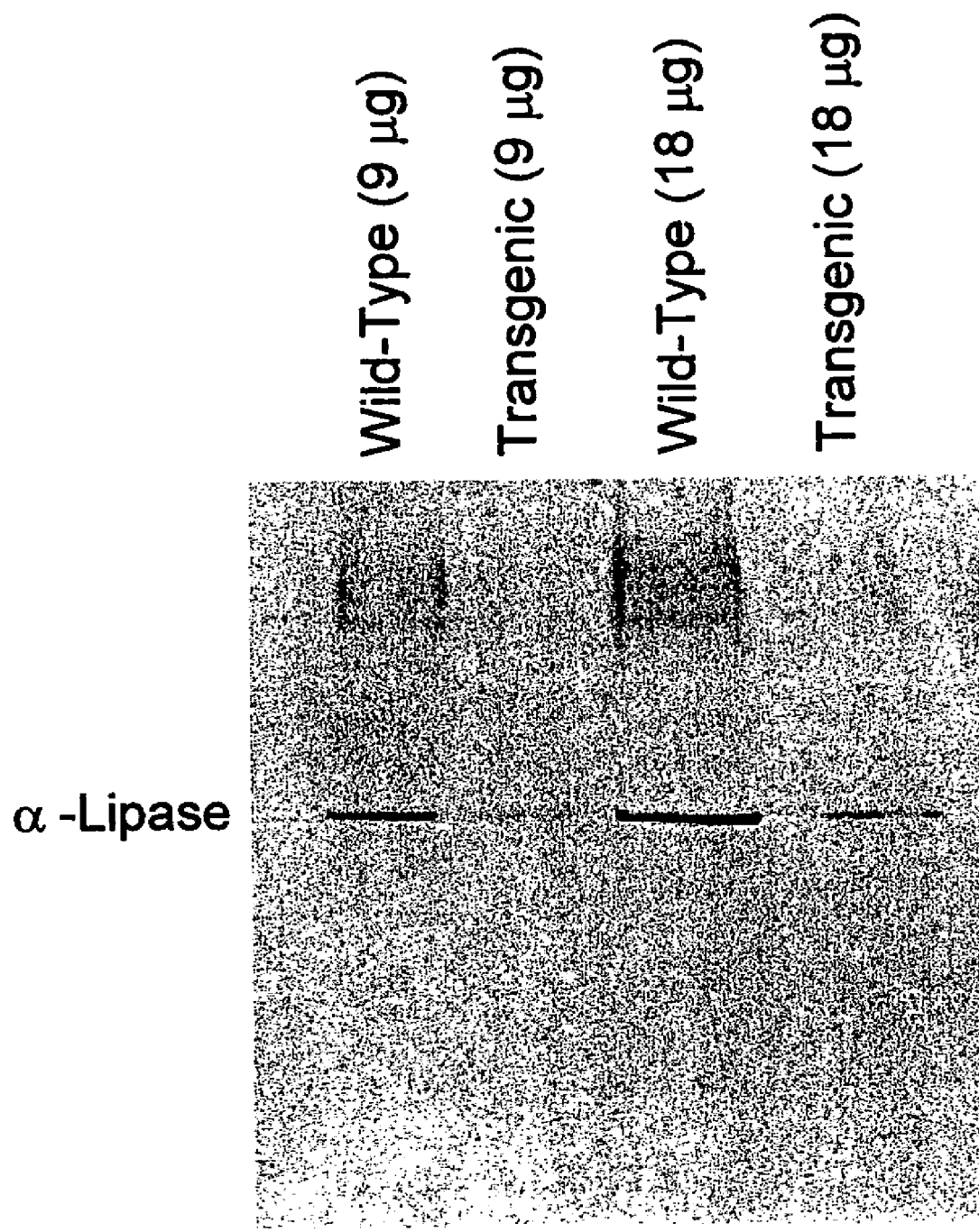

FIG. 21 is a Western blot of total protein isolated from leaves of four week-old *Arabidopsis* wild-type plants and corresponding transgenic plants expressing the full-length senescence-induced lipase gene in antisense orientation. (Lanes 1 and 2 were loaded with 9 μg of protein, and lanes 3 and 4 were loaded with 18 μg of protein). The blot was probed with antibody raised against the *Arabidopsis* senescence-induced lipase protein. The expression of the senescence-induced lipase is reduced in all transgenic plants.

DETAILED DESCRIPTION OF THE INVENTION

Methods and compositions are provided for altering the expression of senescence-induced lipase gene(s) in plant cells. Alteration of expression of the senescence-induced lipase gene(s) in plants results in delayed onset of senescence and improved resistance to environmental stress, thus extending the plant shelf-life and/or growth period.

A full length cDNA sequence encoding a carnation lipase gene exhibiting senescence-induced expression has been isolated from a cDNA library made from RNA of senescing petals of carnation (*Dianthus caryophyllus*) flowers. Polynucleotide probes corresponding to selected regions of the isolated carnation flower lipase cDNA sequence as well as the full length carnation lipase cDNA were used to determine the presence of mRNA encoding the lipase gene in senescing carnation leaves, ripening tomato fruit and senescing green bean leaves, as well as environmentally stressed (chilled) tomato leaves. Primers designed from the carnation lipase cDNA were used to generate a polymerase chain reaction (PCR) product using tomato leaf genomic DNA as template. The PCR product contains a partial open reading frame which encodes a partial protein sequence including the conserved lipase consensus motif, ITFTGHSLGA (SEQ ID NO:3). The tomato nucleotide sequence has 53.4% sequence identity with the carnation senescence-induced lipase sequence and 43.5% identity with *Arabidopsis* lipase sequence. The *Arabidopsis* lipase sequence has 44.3% identity with the carnation nucleotide sequence.

The carnation senescence-induced lipase gene of the present invention was isolated by screening a cDNA expression library prepared from senescing carnation petals with antibodies raised against cytosolic lipid-protein particles, a source of the carnation lipase. A positive full-length cDNA clone corresponding to the carnation senescence-induced lipase gene was obtained and sequenced. The nucleotide sequence of the senescence-induced lipase cDNA clone is shown in SEQ ID NO:1. The cDNA clone encodes a 447 amino acid polypeptide (SEQ ID NO: 2) having a calculated molecular mass of 50.2 kDa. Expression of the cDNA clone in *E. coli* yielded a protein of the expected molecular weight that exhibits acyl hydrolase activity, i.e., the expressed protein hydrolyzes p-nitrophenylpalmitate, phospholipid and triacylglycerol. Based on the expression pattern of the enzyme in developing carnation flowers and the activity of the protein, it is involved in senescence.

An *Arabidopsis* senescence-induced lipase gene of the present invention was also isolated by PCR using a senescing *Arabidopsis* leaf cDNA library as template in the reaction. The nucleotide and derived amino acid sequence of the *Arabidopsis* senescence-induced lipase gene is shown in FIG. 14 (SEQ ID NO:18) Based on the expression pattern of the lipase gene in developing plants, it is involved in senescence.

Figure 4A:
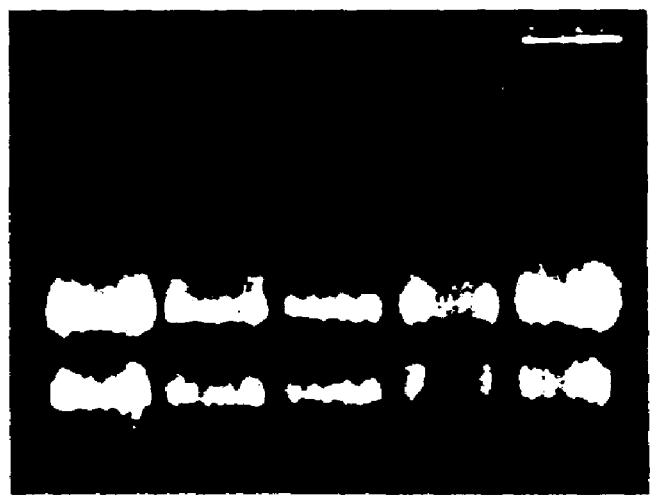
FIG. 4A is the ethidium bromide stained gel of total RNA. Each lane contained 10 μg RNA.
Figure 4B:
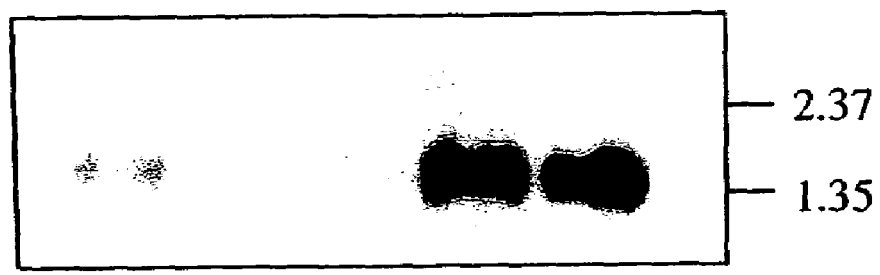
FIG. 4B is an autoradiograph of the Northern blot probed with $^{32}$P-dCTP-labelled full length carnation senescence-induced lipase cDNA.
Figure 11:
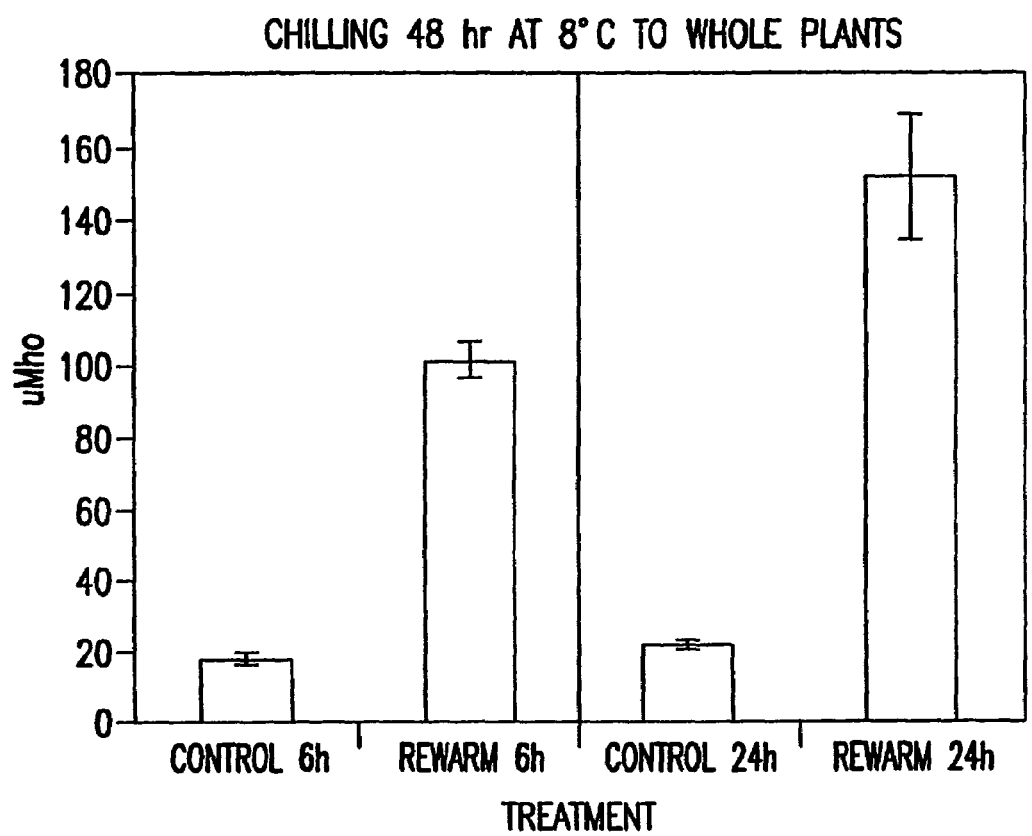
FIG. 11 is a bar graph showing the effects of chilling on membrane leakiness. Tomato plants were chilled at 8° for 48 hours and then rewarmed to room temperature. Diffusate leakage (μMhos) from leaf disks was measured for control plants, which had not been chilled, and for chilled plants for 6 and 24 hour periods.
Figure 12:
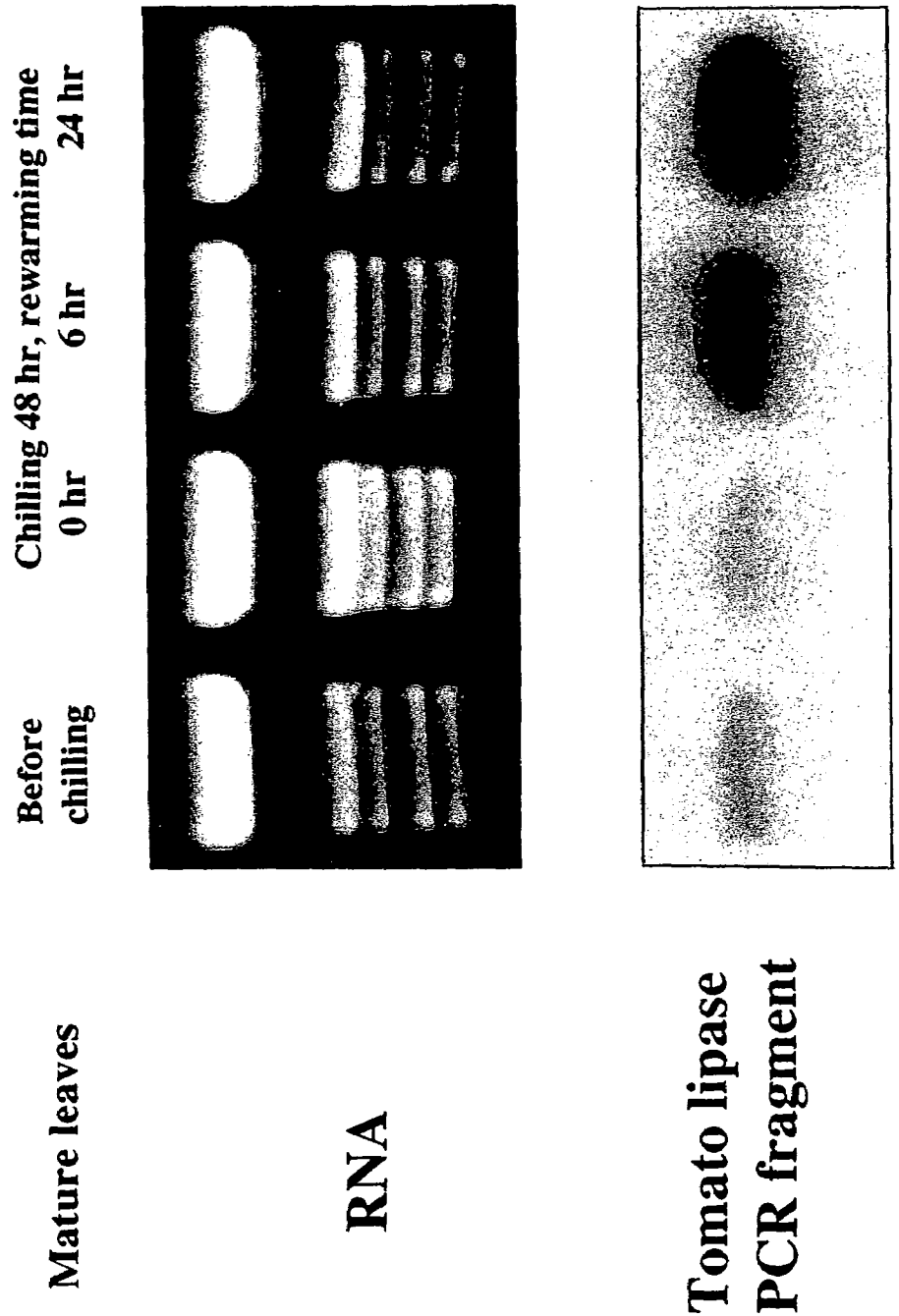
FIG. 12 is a Northern blot analysis of tomato leaf RNA isolated from plants that had been chilled at 8° C. for 48 hours and rewarmed to ambient temperature for 24 hours. Upper Panel is the ethidium bromide stained gel of total leaf RNA. Lower Panel is an autoradiograph of the Northern blot probed with $^{32}$P-dCTP-labelled full length carnation senescence-induced lipase cDNA.

Northern blots of carnation petal total RNA probed with the full length carnation cDNA show that the expression of the senescence-induced lipase gene is significantly induced just prior to the onset of natural senescence (FIG. 4). Northern blot analyses also demonstrate that the senescence-induced lipase gene is induced by environmental stress conditions, e.g., chilling (FIG. 12) and ethylene (FIGS. 4 and 9), which is known to be produced in response to environmental stress. The Northern blot analyses show that the presence of carnation senescence-induced lipase mRNA is significantly higher in senescing (developmental stage IV) than in young stage I, II and III carnation petals. Furthermore, ethylene-stimulated stage II flowers also show higher senescence-induced lipase gene expression. Similarly, plants that have been exposed to chilling temperatures and returned to ambient temperature also show induced expression of the senescence-induced lipase gene coincident with the development of chilling injury symptoms (e.g., leakiness) (FIGS. 11 and 12).

Expression of the *Arabidopsis* senescence-induced lipase gene is similarly regulated. Northern blot analysis of total RNA from leaves of *Arabidopsis* plants at various stages of development show that the lipase gene is upregulated coincident with the onset of leaf senescence. (FIG. 15) Also, like the carnation senescence-induced lipase gene, the *Arabidopsis* senescence-induced lipase gene is upregulated by treatment with ethylene, a plant hormone that induces leaf senescence. (FIG. 16)

The overall pattern of gene expression in various plants, e.g., carnation, green beans, tomato, *Arabidopsis*, and various plant tissues, e.g., leaves, fruit and flowers, demonstrates that the lipase genes of the invention are involved in the initiation of senescence in these plants and plant tissues. Thus, it is expected that by substantially repressing or altering the expression of the senescence-induced lipase genes in plant tissues, senescence, deterioration and spoilage can be delayed, increasing the shelf-life of perishable fruits, flowers and vegetables. This can be achieved by producing transgenic plants in which the lipase cDNA or an oligonucleotide fragment thereof is expressed in the antisense configuration in fruits, flowers, vegetable, agronomic crop plants and forest species, preferably using a constitutive promoter such as the CaMV 35S promoter, or using a tissue-specific or senescence-inducible promoter.

Figure 6A:
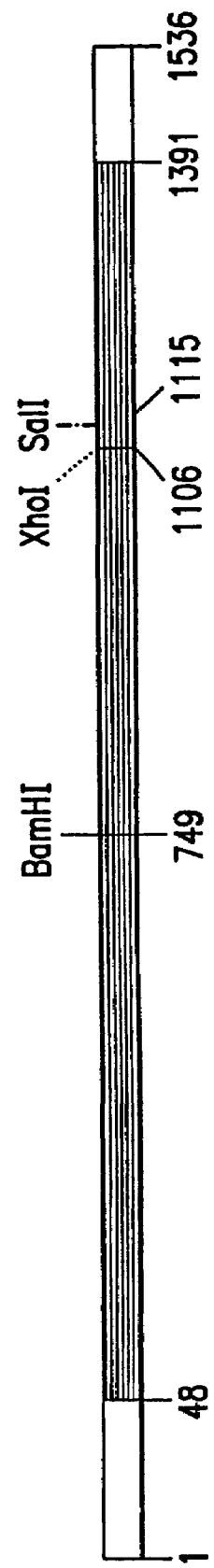
FIG. 6A illustrates a restriction enzyme map of the open reading frame of the carnation senescence-induced lipase. The numbers refer to nucleotides in the open reading frame.
Figure 6B:
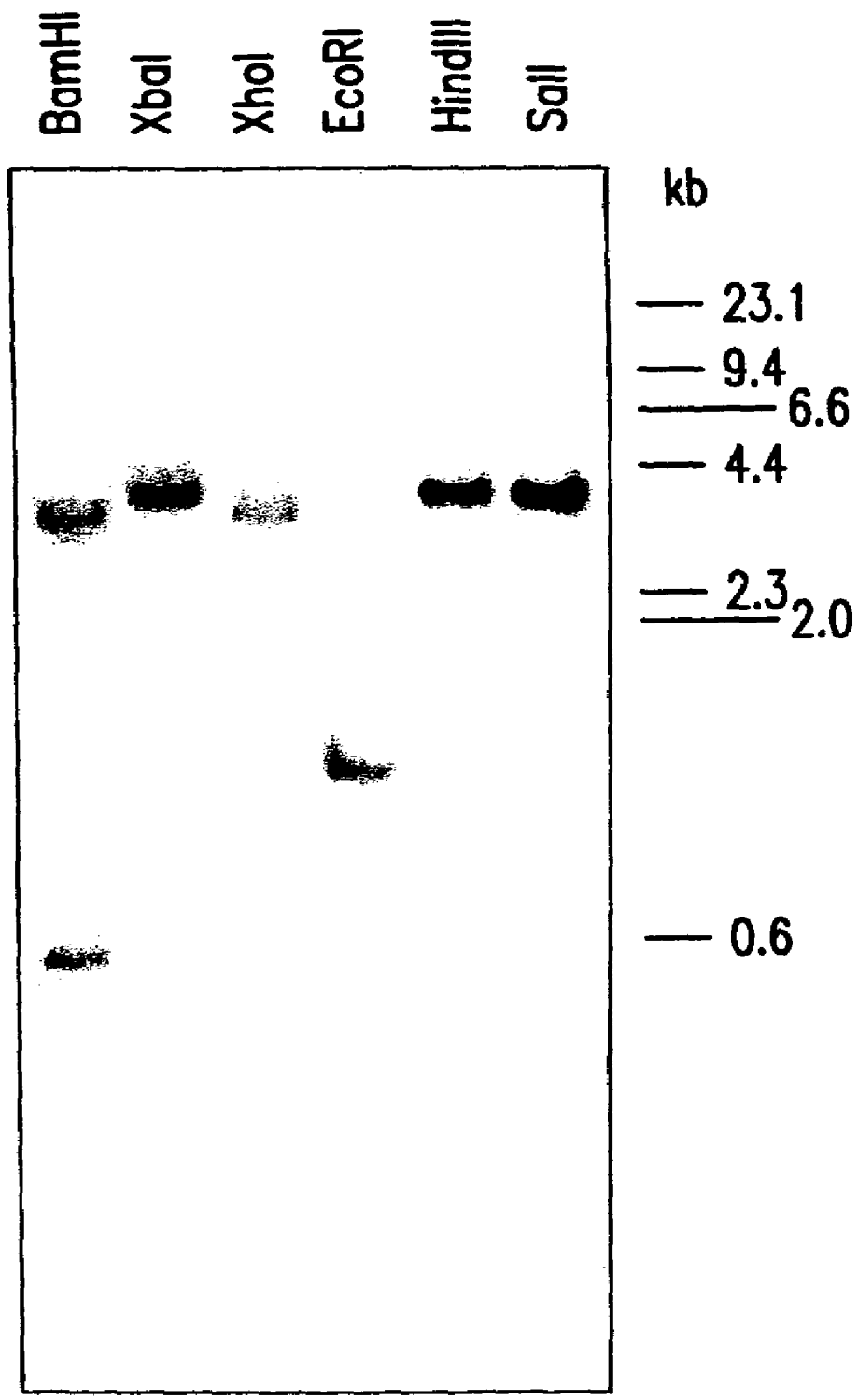
FIG. 6B is a Southern blot analysis of carnation genomic DNA digested with various restriction enzymes and probed with carnation senescence-induced lipase cDNA.

The carnation senescence-induced lipase gene is a single copy gene. Southern blot analysis of carnation genomic DNA cut with various restriction enzymes that do not recognize sequences within the open reading frame of the senescence-induced lipase cDNA was carried out. The restriction enzyme-digested genomic DNA was probed with $^{32}$P-dCTP-labelled full length cDNA (SEQ ID NO:1). Under high stringency hybridization conditions, only one restriction fragment hybridizes to the cDNA clone (68° C. for both hybridization and washing; washing buffer: 0.2%×SSC, 0.1% SDS). Thus, the carnation senescence-induced lipase gene is a single copy gene (FIG. 6). The fact that this gene is not a member of a multigene family in carnations strongly suggests that it is a single copy gene in other plants.

Knowledge of the complete nucleotide sequence of the carnation senescence-induced lipase gene or *Arabidopsis* senescence-induced lipase gene is sufficient for the isolation of the senescence-induced lipase gene(s) from various other plant species. Indeed, as demonstrated herein, oligonucleotide primers based on the carnation cDNA sequence have been successfully used to generate tomato leaf senescence-induced lipase gene fragments by polymerase chain reactions using tomato leaf genomic DNA as template.

The cloned senescence-induced lipase gene(s) or fragment(s) thereof, alone or in combination, when introduced in reverse orientation (antisense) under control of a constitutive promoter, such as the fig wart mosaic virus 35S promoter, the cauliflower mosaic virus promoter CaMV35S or the MAS promoter, can be used to genetically modify plants and alter senescence in the modified plants. Selected antisense sequences from other plants which share sufficient sequence identity with the carnation senescence-induced lipase gene can be used to achieve similar genetic modification. One result of the genetic modification is a reduction in the amount of endogenous translatable senescence-induced lipase-encoding mRNA. Consequently, the amount of senescence-induced lipase produced in the plant cells is reduced, thereby reducing the amount of cell membrane damage and cell leakage, e.g., reduced leaf, fruit and/or flower senescence and spoilage, due to aging or environmental stress.

For example, *Arabidopsis* plants transformed with vectors that express the full-length *Arabidopsis* senescence-induced lipase gene in antisense orientation, under regulation of double 35S promoter exhibit larger leaf size and overall larger plant growth as compared to wild-type plants as shown in FIGS. 17 and 18. These plants also demonstrate delayed leaf senescence, as shown in FIG. 19.

The effect of reduced expression of the senescence-induced lipase gene brought about by expressing the full-length lipase gene in antisense orientation in transgenic *Arabidopsis* plants is also seen as an increase in seed yield in the transformed plants. *Arabidopsis* plant lines expressing the full-length senescence-induced lipase gene produce up to about two to three times more seed than wild type plants. (FIG. 20)

That the effects observed in transgenic plants on biomass, leaf senescence and seed yield are due to a decrease in senescence-induced lipase in these plants is shown in FIG. 21. The transgenic plants of the invention exhibit significantly reduced expression of senescence-induced lipase in comparison to wild-type plants.

Thus, the methods and sequences of the present invention can be used to delay plant spoilage, including leaf or fruit spoilage, as well as to increase plant biomass and seed yield, and in general, alter senesence in plants.

The isolated nucleotide sequences of this invention can be used to isolate substantially complementary senescence-induced lipase nucleotide sequence from other plants or organisms. These sequences can, in turn, be used to transform plants and thereby alter senescence of the transformed plants in the same manner as shown with the use of the isolated nucleotide sequences shown herein.

The genetic modifications observed with transformation of plants with senescence-induced lipase, functional fragments thereof or combinations thereof can effect a permanent change in levels of senescence-induced lipase in the plant and be propagated in offspring plants by selfing or other reproductive schemes. The genetically altered plant is used to produce a new line of plants wherein the alteration is stably transmitted from generation to generation. The present invention provides for the first time the appropriate DNA sequences which may be used to achieve a stable genetic modification of senescence in a wide range of different plants.

For the identification and isolation of the senescence-induced lipase gene, in general, preparation of plasmid DNA, restriction enzyme digestion, agarose gel electrophoresis of DNA, polyacrylamide gel electrophoresis of protein, Southern blots, Northern blots, DNA ligation and bacterial transformation were carried out using conventional methods well-known in the art. See, for example, Sambrook, J. et al., Molecular Cloning: A Laboratory Manual, 2nd ed., Cold Spring Harbor Press, Cold Spring Harbor, N.Y., 1989. Techniques of nucleic acid hybridization are disclosed by Sambrook (Supra).

As used herein, the term "plant" refers to either a whole plant, a plant part, a plant cell or a group of plant cells. The type of plant which can be used in the method of the invention is not limited and includes, for example, ethylene-sensitive and ethylene-insensitive plants; fruit bearing plants such as apricots, apples, oranges, bananas, grapefruit, pears, tomatoes, strawberries, avocados, etc.; vegetables such as carrots, peas, lettuce, cabbage, turnips, potatoes, broccoli, asparagus, etc.; flowers such as carnations, roses, mums, etc.; and in general, any plant that can take up and express the DNA molecules of the present invention. It may include plants of a variety of ploidy levels, including haploid, diploid, tetraploid and polyploid.

A transgenic plant is defined herein as a plant which is genetically modified in some way, including but not limited to a plant which has incorporated heterologous or homologous senescence-induced lipase DNA or modified DNA or some portion of heterologous senescence-induced lipase DNA or homologous senescence-induced lipase DNA into its genome. The altered genetic material may encode a protein, comprise a regulatory or control sequence, or may be or include an antisense sequence or encode an antisense RNA which is antisense to the endogenous senescence-induced lipase DNA or mRNA sequence or portion thereof of the plant. A "transgene" or "transgenic sequence" is defined as a foreign gene or partial sequence which has been incorporated into a transgenic plant.

The term "hybridization" as used herein is generally used to mean hybridization of nucleic acids at appropriate conditions of stringency as would be readily evident to those skilled in the art depending upon the nature of the probe sequence and target sequences. Conditions of hybridization and washing are well known in the art, and the adjustment of conditions depending upon the desired stringency by varying incubation time, temperature and/or ionic strength of the solution are readily accomplished. See, for example, Sambrook, J. et al., Molecular Cloning: A Laboratory Manual, 2nd edition, Cold spring harbor Press, Cold Spring harbor, N.Y., 1989. The choice of conditions is dictated by the length of the sequences being hybridized, in particular, the length of the probe sequence, the relative G-C content of the nucleic acids and the amount of mismatches to be permitted. Low stringency conditions are preferred when partial hybridization between strands that have lesser degrees of complementarity is desired. When perfect or near perfect complementarity is desired, high stringency conditions are preferred. For typical high stringency conditions, the hybridization solution contains 6×S.S.C., 0.01 M EDTA, 1× Denhardt's solution and 0.5% SDS. Hybridization is carried out at about 68° C. for about 3 to 4 hours for fragments of cloned DNA and for about 12 to about 16 hours for total eukaryotic DNA. For lower stringencies the temperature of hybridization is reduced to about 12° C. below the melting temperature ($T_M$) of the duplex. The $T_M$ is known to be a function of the G-C content and duplex length as well as the ionic strength of the solution.

As used herein, the term "substantial sequence identity" or "substantial homology" is used to indicate that a nucleotide sequence or an amino acid sequence exhibits substantial structural or functional equivalence with another nucleotide or amino acid sequence. Any structural or functional differences between sequences having substantial sequence identity or substantial homology will be de minimis; that is, they will not affect the ability of the sequence to function as indicated in the desired application. Differences may be due to inherent variations in codon usage among different species, for example. Structural differences are considered de minimis if there is a significant amount of sequence overlap or similarity between two or more different sequences or if the different sequences exhibit similar physical characteristics even if the sequences differ in length or structure. Such characteristics include for example, ability to hybridize under defined conditions, or in the case of proteins, immunological crossreactivity, similar enzymatic activity, etc.

Additionally, two nucleotide sequences are "substantially complementary" if the sequences have at least about 40 percent, more preferably, at least about 60 percent and most preferably about 90 percent sequence similarity between them. Two amino acid sequences are substantially homologous if they have at least 40%, preferably 70% similarity between the active portions of the polypeptides.

As used herein, the phrase "hybridizes to a corresponding portion" of a DNA or RNA molecule means that the molecule that hybridizes, e.g., oligonucleotide, polynucleotide, or any nucleotide sequence (in sense or antisense orientation) recognizes and hybridizes to a sequence in another nucleic acid molecule that is of approximately the same size and has enough sequence similarity thereto to effect hybridization under appropriate conditions. For example, a 100 nucleotide long antisense molecule from the 3' coding or non-coding region of carnation lipase will recognize and hybridize to an approximately 100 nucleotide portion of a nucleotide sequence within the 3' coding or non-coding region, respectively of the *Arabidopsis* senescence-induced lipase gene or any other plant senescence-induced lipase gene so long as there is about 70% or more sequence similarity between the two sequences. It is to be understood that the size of the "corresponding portion" will allow for some mismatches in hybridization such that the "corresponding portion" may be smaller or larger than the molecule which hybridizes to it, for example 20–30% larger or smaller, preferably no more than about 12–15% larger or smaller.

The term "functional derivative" of a nucleic acid (or poly- or oligonucleotide) is used herein to mean a fragment, variant, homolog, or analog of the gene or nucleotide sequence encoding senescence-induced lipase. A functional derivative may retain at least a portion of the function of the senescence-induced lipase encoding DNA which permits its utility in accordance with the invention. Such function may include the ability to hybridize with native carnation senescence-induced lipase or substantially homologous DNA from another plant which encodes senescence-induced lipase or with an mRNA transcript thereof, or, in antisense orientation, to inhibit the transcription and/or translation of plant senescence-induced lipase mRNA, or the like.

A "fragment" of the gene or DNA sequence refers to any subset of the molecule, e.g., a shorter polynucleotide or oligonucleotide. A "variant" refers to a molecule substantially similar to either the entire gene or a fragment thereof, such as a nucleotide substitution variant having one or more substituted nucleotides, but which maintains the ability to hybridize with the particular gene or to encode mRNA transcript which hybridizes with the native DNA. A "homolog" refers to a fragment or variant sequence from a different plant genus or species. An "analog" refers to a non-natural molecule substantially similar to or functioning in relation to either the entire molecule, a variant or a fragment thereof.

By "altered expression" or "modified expression" of a gene, e.g., the senescence-induced lipase gene, is meant any process or result whereby the normal expression of the gene, for example, that expression occurring in an unmodified carnation or other plant, is changed in some way. As intended herein, alteration in gene expression is complete or partial reduction in the expression of the senescence-induced lipase gene, but may also include a change in the timing of expression, or another state wherein the expression of the senescence-induced lipase gene differs from that which would be most likely to occur naturally in an unmodified plant or cultivar. A preferred alteration is one which results in reduction of senescence-induced lipase production by the plant compared to production in an unmodified plant.

In producing a genetically altered plant in accordance with this invention, it is preferred to select individual plantlets or plants by the desired trait, generally reduced senescence-induced lipase expression or production. Expression of senescence-induced lipase can be quantitated, for example in a conventional immunoassay method using a specific antibody as described herein. Also, senescence-induced lipase enzymatic activity can be measured using biochemical methods as described herein.

In order for a newly inserted gene or DNA sequence to be expressed, resulting in production of the protein which it encodes, or in the case of antisense DNA, to be transcribed, resulting in an antisense RNA molecule, the proper regulatory elements should be present in proper location and orientation with respect to the gene or DNA sequence. The regulatory regions may include a promoter, a 5'-non-translated leader sequence and a 3'-polyadenylation sequence as well as enhancers and other regulatory sequences.

Promoter regulatory elements that are useful in combination with the senescence-induced lipase gene to generate sense or antisense transcripts of the gene include any plant promoter in general, and more particularly, a constitutive promoter such as the fig wart mosaic virus 35S promoter, double 35S promoter, the cauliflower mosaic virus promoter, CaMV35S promoter, or the MAS promoter, or a tissue-specific or senescence-induced promoter, such as the carnation petal GST1 promoter or the *Arabidopsis* SAG12 promoter (See, for example, J. C. Palaqui et al., Plant Physiol., 112:1447–1456 (1996); Morton et al., Molecular Breeding, 1:123–132 (1995); Fobert et al., Plant Journal, 6:567–577 (1994); and Gan et al., Plant Physiol., 113:313 (1997), incorporated herein by reference). Preferably, the promoter used in the present invention is a constitutive promoter.

Expression levels from a promoter which is useful for the present invention can be tested using conventional expression systems, for example by measuring levels of a reporter gene product, e.g., protein or mRNA in extracts of the leaves, flowers, fruit or other tissues of a transgenic plant into which the promoter/reporter have been introduced.

The present invention provides antisense oligonucleotides and polynucleotides complementary to the gene encoding carnation senescence-induced lipase, complementary to the gene encoding *Arabidopsis* senescence-induced lipase or complementary to a gene or gene fragment from another plant, which hybridizes with the carnation or *Arabidopsis* senescence-induced lipase gene under low to high stringency conditions. Such antisense oligonucleotides should be at least about six nucleotides in length to provide minimal specificity of hybridization and may be complementary to one strand of DNA or mRNA encoding senescence-induced lipase or a portion thereof, or to flanking sequences in genomic DNA which are involved in regulating senescence-induced lipase gene expression. The antisense oligonucleotide may be as large as 100 nucleotides and may extend in length up to and beyond the full coding sequence for which it is antisense. The antisense oligonucleotides can be DNA or RNA or chimeric mixtures of DNA and RNA or derivatives or modified versions thereof, single stranded or double stranded.

The action of the antisense oligonucleotide may result in alteration, primarily inhibition, of senescence-induced lipase gene expression in cells. For a general discussion of antisense see: Alberts, et al., Molecular Biology of the Cell, 2nd ed., Garland Publishing, Inc. New York, N.Y. (1989, in particular pages 195–196, incorporated herein by reference).

The antisense oligonucleotide may be complementary to any portion of the senescence-induced lipase gene. In one embodiment, the antisense oligonucleotide may be between 6 and 100 nucleotides in length, and may be complementary to the 5'-non-coding sequence or 3'end of the senescence-induced lipase sequence, for example. Antisense oligonucleotides primarily complementary to 5'-non-coding sequences are known to be effective inhibitors of expression of genes encoding transcription factors. Branch, M. A., Molec. Cell Biol., 13:4284–4290 (1993).

Preferred antisense oligonucleotides are substantially complementary to a corresponding portion of the mRNA encoding senescence-induced lipase. For example, introduction of the full length cDNA clone encoding senescence-induced lipase in an antisense orientation into a plant is expected to result in successful altered senescence-induced lipase gene expression. Moreover, introduction of partial sequences, targeted to specific portions of the senescence-induced lipase gene, can be equally effective.

The minimal amount of homology required by the present invention is that sufficient to result in sufficient complementarity to provide recognition of the specific target RNA or DNA and inhibition or reduction of its translation or function while not affecting function of other RNA or DNA molecules and the expression of other genes. While the antisense oligonucleotides of the invention comprise sequences complementary to at least a portion of an RNA transcript of the senescence-induced lipase gene, absolute complementarity, although preferred is not required. The ability to hybridize may depend on the length of the antisense oligonucleotide and the degree of complementarity. Generally, the longer the hybridizing nucleic acid, the more base mismatches with the senescence-induced lipase target sequence it may contain and still form a stable duplex. One skilled in the art can ascertain a tolerable degree of mismatch by use of standard procedures to determine the melting temperature of the hybridized complex, for example.

The antisense RNA oligonucleotides may be generated intracellularly by transcription from exogenously introduced nucleic acid sequences. The antisense molecule may be delivered to a cell by transformation or transfection or infection with a vector, such as a plasmid or virus into which is incorporated DNA encoding the antisense senescence-induced lipase sequence operably linked to appropriate regulatory elements, including a promoter. Within the cell the exogenous DNA sequence is expressed, producing an antisense RNA of the senescence-induced lipase gene.

Vectors can be plasmids, preferably, or may be viral or other vectors known in the art to replicate and express genes encoded thereon in plant cells or bacterial cells. The vector becomes chromosomally integrated such that it can be transcribed to produce the desired antisense senescence-induced lipase RNA. Such plasmid or viral vectors can be constructed by recombinant DNA technology methods that are standard in the art. For example, the vector may be a plasmid vector containing a replication system functional in a prokaryotic host and an antisense oligonucleotide or polynucleotide according to the invention. Alternatively, the vector may be a plasmid containing a replication system functional in *Agrobacterium* and an antisense oligonucleotide or polynucleotide according to the invention. Plasmids that are capable of replicating in *Agrobacterium* are well known in the art. See, Miki, et al., Procedures for Introducing Foreign DNA Into Plants, Methods in Plant Molecular Biology and Biotechnology, Eds. B. R. Glick and J. E. Thompson. CRC Press (1993), PP. 67–83.

The carnation lipase gene was cloned in the antisense orientation into a plasmid vector in the following manner. The pCD plasmid, which is constructed from a pUC18 backbone and contains the 35S promoter from cauliflower mosaic virus (CaMV) followed by a multiple cloning site and an octapine synthase termination sequence was used for cloning the carnation lipase gene. The pcd-lipase (antisense) plasmid was constructed by subcloning the full length carnation lipase gene in the antisense orientation into a Hind3 site and EcoR1 site of pCd. Similarly, a pCDA35S-GST1-lipase (antisense) plasmid was constructed by first subcloning a PCR amplified fragment (−703 to +19 bp) of the carnation Glutathione S Transferase 1 (GST1) promoter into the BamH1 and Sal1 sites of the pCd vector. The full length carnation lipase gene was then subcloned in the antisense orientation into the Hind3 and EcoR1 sites of the construct. Another plasmid, pGdΔ35S-GST1-GUS plasmid, was constructed by first subcloning a PCR-amplified fragment (−703 to +19 bp) of the carnation Glutathione S-Transferase 1 (GST1) promoter into the BamH1 and Sal1 sites of the pCd vector. The reporter gene beta-glucuronidase (GUS) was then subcloned into the Sal1 and EcoRI sites of the construct. The pCd-35S²-lipase (antisense) plasmid was constructed by first subcloning a double 35S promoter (containing two copies of the CaMV 35S promoter in tandem) into the Sma1 and Hind3 sites of the pCd vector. The full length carnation lipase gene was then subcloned in the antisense orientation into the Hind3 and EcoR1 sites of the construct.

An oligonucleotide, preferably between about 6 and about 100 nucleotides in length and complementary to the target sequence of senescence-induced lipase, may be prepared by recombinant nucleotide technologies or may be synthesized from mononucleotides or shorter oligonucleotides, for example. Automated synthesizers are applicable to chemical synthesis of the oligo- and polynucleotides of the invention. Procedures for constructing recombinant nucleotide molecules in accordance with the present invention are disclosed in Sambrook, et al., In: Molecular Cloning: A Laboratory Manual, 2nd ed., Cold Spring Harbor Press, Cold Spring Harbor, N.Y. (1989), which is incorporated herein in its entirety. Oligonucleotides which encode antisense RNA complementary to senescence-induced lipase sequence can be prepared using procedures well known to those in the art. Details concerning such procedures are provided in Maniatis, T. et al., Molecular mechanisms in the Control of Gene expression, eds., Nierlich, et al., eds., Acad. Press, N.Y. (1976).

In an alternative embodiment of the invention, inhibition of expression of endogenous plant senescence-induced lipase is the result of co-suppression through over-expression of an exogenous senescence-induced lipase gene or gene fragment introduced into the plant cell. In this embodiment of the invention, a vector encoding senescence-induced lipase in the sense orientation is introduced into the cells in the same manner as described herein for antisense molecules. Preferably, the senescence-induced lipase is operatively linked to a strong constitutive promoter, such as for example the fig wart mosaic virus promoter or CaMV35S.

Transgenic plants made in accordance with the present invention may be prepared by DNA transformation using any method of plant transformation known in the art. Plant transformation methods include direct co-cultivation of plants, tissues or cells with *Agrobacterium tumerfaciens* or direct infection (Miki, et al., Meth. in Plant Mol. Biol. and Biotechnology, (1993), p. 67–88); direct gene transfer into protoplasts or protoplast uptake (Paszkowski, et al., EMBO J., 12:2717 (1984); electroporation (Fromm, et al., Nature, 319:719 (1986); particle bombardment (Klein et al., Bio-Technology, 6:559–563 (1988); injection into meristematic tissues of seedlings and plants (De LaPena, et al., Nature, 325:274–276 (1987); injection into protoplasts of cultured cells and tissues (Reich, et al., BioTechnology, 4:1001–1004 (1986)).

Generally a complete plant is obtained from the transformation process. Plants are regenerated from protoplasts, callus, tissue parts or explants, etc. Plant parts obtained from the regenerated plants in which the expression of senescence-induced lipase is altered, such as leaves, flowers, fruit, seeds and the like are included in the definition of "plant" as used herein. Progeny, variants and mutants of the regenerated plants are also included in the definition of "plant."

The present invention also provides carnation or *Arabidopsis* senescence-induced lipase protein encoded by the cDNA molecules of the invention and proteins which cross-react with antibody to the carnation or *Arabidopsis* protein. Such proteins have the amino acid sequence set forth in SEQ ID No:2, shown in FIG. 1, share cross reactivity with antibodies to the protein set forth in SEQ ID NO:2, have the amino acid sequence set forth in SEQ ID NO:19 (shown in FIG. 14) or share cross reactivity with antibodies to the protein set forth in SEQ ID NO:19.

Figure 3:
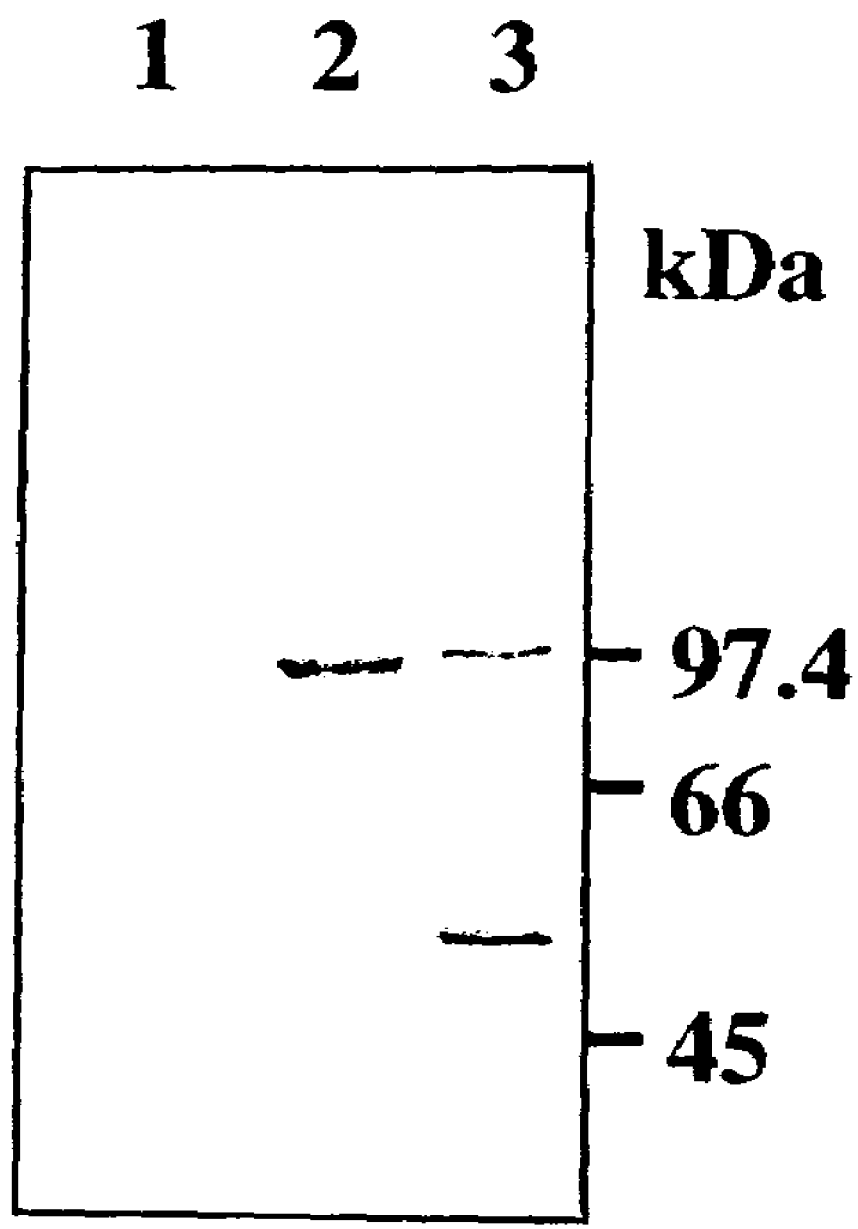
FIG. 3 shows a Western blot analysis of the fusion protein expression product obtained from carnation lipase cDNA expressed in *E. coli*. The Western blot was probed with antibodies to the senescence-induced lipase protein. Lane 1, maltose binding protein; lane 2, fusion protein consisting of carnation lipase fused through a proteolytic (Factor Xa) cleavage site to maltose binding protein cDNA; lane 3, fusion protein partially cleaved with Factor Xa into free lipase protein (50.2 kda) and free maltose-binding protein.

The carnation or *Arabidopsis* senescence-induced lipase protein or functional derivatives thereof are preferably produced by recombinant technologies, optionally in combination with chemical synthesis methods. In one embodiment of the invention the senescence-induced lipase is expressed as a fusion protein consisting of the senescence-induced lipase fused with maltose binding protein. Expression of a clone encoding the recombinant fusion protein yields a fusion protein of the expected molecular weight that hydrolyzes p-nitrophenylpalmitate, phospholipid and triacylglycerol, which is an indicator of lipase activity. The recombinant senescence-induced lipase protein shows a predominant band in Western blot analyses after immunoblotting with antibody to carnation senescence-induced lipase. The free senescence-induced lipase (50.2 Kda), which is released by treatment of the fusion protein with the protease, factor Xa, also reacts with the senescence-induced lipase antibody in Western blot analysis (FIG. 3). A motif search of the senescence-induced lipase amino acid sequence shows the presence of a potential N-myristoylation site (FIG. 1) for the covalent attachment of myristate via an amide linkage (See Johnson, et al., Ann. Rev. Biochem., 63: 869–914 (1994); Towler, et al., Ann. Rev. Biochem., 57:67–99 (1988); and R. J. A. Grand, Biochem. J., 258:625–638 (1989). The protein motif search also showed that the carnation senescence-induced lipase contains a sequence, ITFAGHSLGA, (SEQ ID NO:4) which is the conserved lipase consensus sequence (Table 1). The conserved lipase consensus sequence from a variety of plants is shown in the table below.

TABLE 1

| Plant Species | conserved Lipase Sequence |
|---|---|
| Carnation | I T F A G H S L G A (SEQ ID NO: 4) |
| Tomato | I T F T G H S L G A (SEQ ID NO: 3) |
| Arabidopsis | I T T C G H S L G A (SEQ ID NO: 9) |
| Ipomoea nil | I T V T G H S L G S (SEQ ID NO: 10) |

The senescence-induced lipase protein of the invention was shown to possess lipase activity in both in vitro and in situ assays. For in vitro measurements, p-nitrophenylpalmitate and soybean phospholipid (40% phosphatidylcholine and 60% other phospholipids) were used as substrates, and the products of the reactions, p-nitrophenol and free fatty acids, respectively, were measured spectrophotometrically (Pencreac'h and Baratti, 1996; Nixon and Chan, 1979; Lin et al., 1983). Lipase activity was also measured in vitro by gas chromatography using a modification of the method described by Nixon and Chan (1979) and Lin et al. (1983). The reaction mixture contained 100 mM Tris-HCl (pH 8.0), 2.5 mM substrate (trilinolein, soybean phospholipid or dilinoleylphosphatidylcholine) and enzyme protein (100 µg) in a final volume of 100 µl. The substrates were emulsified in 5% gum arabic prior to being added to the reaction mixture.

To achieve this, the substrates were dissolved in chloroform, added to the gum arabic solution and emulsified by sonication for 30 s. After emulsification, the chloroform was evaporated by a stream of $N_2$. The reaction was carried out at 25° C. for varying periods of time up to 2 hours. The reaction mixture was then lipid-extracted, and the free fatty acids were purified by TLC, derivitized and quantified by GC (McKegney et al., 1995).

Figure 5:
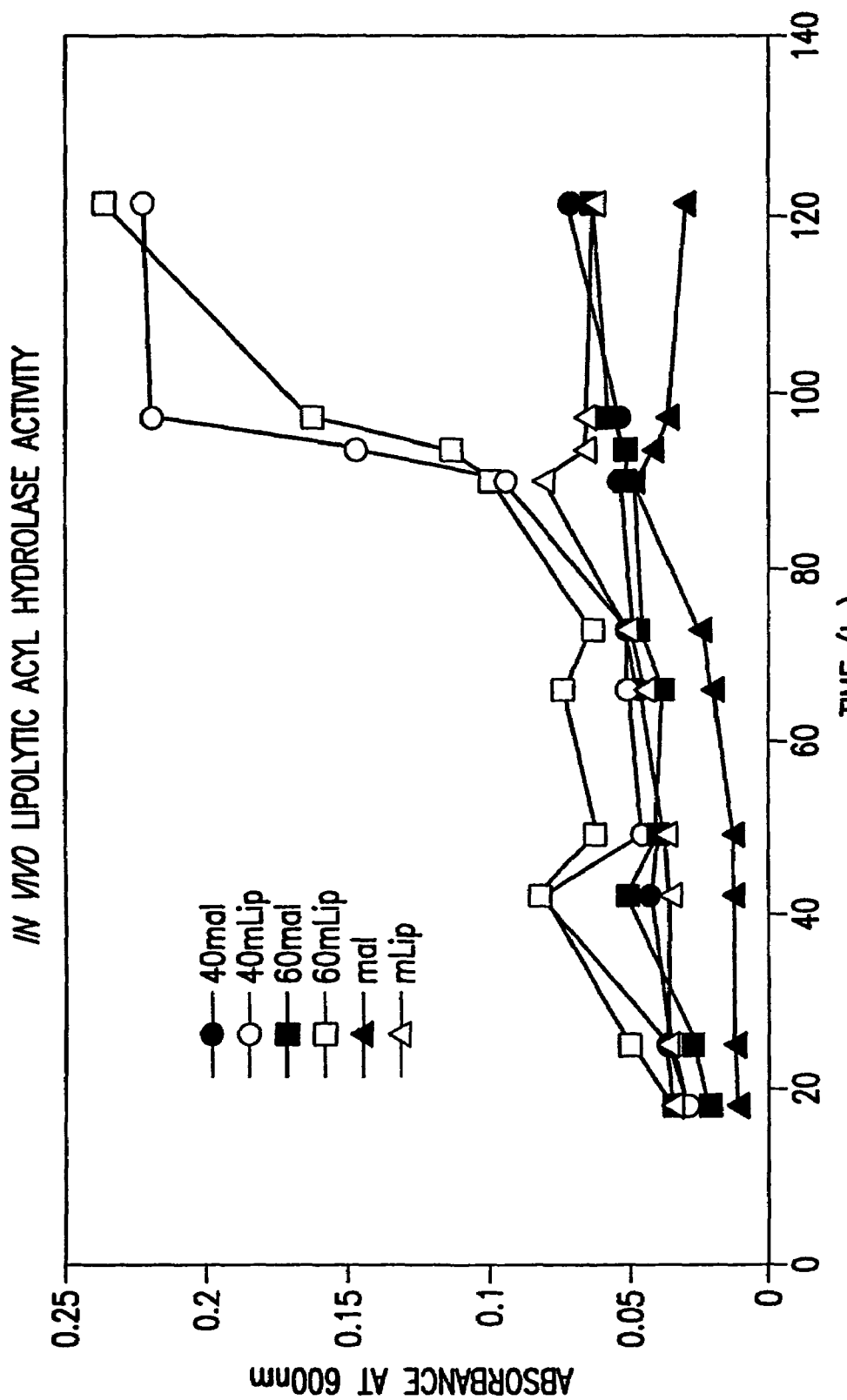
FIG. 5 is an in situ demonstration of lipolytic acyl hydrolase, i.e., lipase activity of the protein product obtained by over expression of the carnation senescence-induced lipase cDNA in *E. coli*. mal, *E. coli* cells containing maltose binding protein alone in a basal salt medium; mLip, *E. coli* cells containing the fusion protein consisting of the carnation senescence-induced lipase fused with maltose binding protein in basal salt medium; 40 mal/40 mLip, *E. coli* cells containing maltose binding protein alone [mal] or the lipase-maltose binding protein fusion product [mLip] in basal salt medium supplemented with Tween 40; 60 mal/60 mLip, *E. coli* cells containing maltose binding protein alone [mal] or the lipase-maltose binding protein fusion product [mLip] in basal salt medium supplemented with Tween 60.

Lipolytic acyl hydrolase activity was measure in situ as described by Furukawa et al. (1983) and modified by Tsuboi et al. (1996). In this latter assay, *E. coli* transformed with the full length cDNA clone encoding senescence-induced lipase were grown in minimal salt medium supplemented with Tween 40 or Tween 60, both of which are long chain fatty acid esters, as the only source of carbon. Thus, carbon for bacterial growth was only available if the fatty acid esters were hydrolyzed by lipase. The finding that *E. coli* transformed with the scenescence-induced lipase cDNA grow in Tween 40- and Tween 60-basal medium after an initial lag phase, whereas control cultures of *E. coli* that were not transformed do not grow, confirms the lipase activity of the encoded recombinant protein (FIG. 5). That is, the senescence-induced lipase releases stearate (Tween 60) and palmitate (Tween 40) to obtain the necessary carbon for growth.

"Functional derivatives" of the senescence-induced lipase protein as described herein are fragments, variants, analogs, or chemical derivatives of senescence-induced lipase, which retain at least a portion of the senescence-induced lipase activity or immunological cross reactivity with an antibody specific for senescence-induced lipase. A fragment of the senescence-induced lipase protein refers to any subset of the molecule. Variant peptides may be made by direct chemical synthesis, for example, using methods well known in the art. An analog of senescence-induced lipase refers to a non-natural protein substantially similar to either the entire protein or a fragment thereof. Chemical derivatives of senescence-induced lipase contain additional chemical moieties not normally a part of the peptide G38 or peptide fragment. Modifications may be introduced into the senescence-induced lipase peptide or fragment thereof by reacting targeted amino acid residues of the peptide with an organic derivatizing agent that is capable of reacting with selected side chains or terminal residues.

A senescence-induced lipase protein or peptide according to the invention may be produced by culturing a cell transformed with a nucleotide sequence of this invention (in the sense orientation), allowing the cell to synthesize the protein and then isolating the protein, either as a free protein or as a fusion protein, depending on the cloning protocol used, from either the culture medium or from cell extracts. Alternatively, the protein can be produced in a cell-free system. Ranu, et al., Meth. Enzymol., 60:459–484, (1979).

Having now generally described the invention, the same will be more readily understood through reference to the following examples which are provided by way of illustration, and are not intended to be limiting to the present invention.

EXAMPLE 1

Plant Materials used to Isolate the Carnation Lipase cDNA

Carnation plants (*Dianthus caryophyllus* L. cv. Improved white Sim) grown and maintained in a greenhouse were used to isolate the nucleotide sequence corresponding to the senescence-induced lipase gene. Flower tissue in the form of senescing flower petals (from different developmental stages) was collected in buffer or stored at −70° C. until used.

Cytosolic lipid particles were isolated from carnation flower petals harvested just before the onset of senescence. Carnation petals (25 g/150 ml buffer) were homogenized at 4° C. in homogenization buffer (50 mM Epps-0.25 M sorbitol pH 7.4, 10 mm EDTA, 2 mM EGTA, 1 mM PMSF, 1 mM benzamadine, 10 mm amino-n-caproic acid and 4% polyvinylpolypyrrolidone) for 45 seconds in an Omnimizer and for an additional minute in a Polytron homogenizer. The homogenate was filtered through four layers of cheesecloth, and the filtrate was centifuged at 10,000 g for twenty minutes at 4° C. The supernatant was centrifuged for one hour at 250,000 g to isolate microsomal membranes. The lipid particles were obtained from the post-microsomal supernatant by collecting the particles after floatation centrifugation by the method of Hudak and Thompson, (1997), Physiol. Plant., 114:705–713. The supernatant was made 10% (w/v) with sucrose, and 23 ml of the supernatant were poured into 60 Ti Beckman centrifuge tubes, overlayed with 1.5 ml isolation buffer and centrifuged at 305,000 g for 12 hours at 4° C. The particles were removed from the isolation buffer overlayer with a Pasteur pipette. Three ml of particle suspension were loaded onto a Sepharose G-25 column equilibrated with sterile PBS (10 mM sodium phosphate buffer pH 7.5 plus 0.85% sodium chloride) and the suspension was eluted with sterile PBS. The void volume containing the particles was eluted and concentrated using a Centricon-10 filter (available from Amicon) to a protein concentration of 600 μg. The lipid particles were then used to generate antibodies in rabbits inoculated with 300 μg of the particles. The IgG titer of the blood was tested by Western blot analysis.

Messenger RNA (mRNA) Isolation

Total RNA was isolated from petals of stage I, II, III or IV carnation flowers essentially as described by Chomczynski and Sachi, Anal. Biochem., 162:156–159 (1987). Briefly, 15 g of petal tissue were frozen in liquid nitrogen and homogenized for 30 seconds in buffer containing 4 M guanidinium thiocyanate, 25 mM sodium citrate, pH 7.0, 0.5% sarkosyl and 0.1 M β-mercaptoethanol. 150 ml water-saturated phenol, 30 ml of chloroform and 15 ml of 2 M NaOAc, pH 4.0 were added to the homogenized sample. The sample was centrifuged at 10,000 g for ten minutes and the aqueous phase removed and nucleic acids precipitated therefrom with 150 ml isopropanol. The sample was centrifuged for ten minutes at 5,000 g and the pellet was washed once with 30 ml of 4 M LiCl, extracted with 30 ml chloroform and precipitated with 30 ml isopropanol containing 0.2 M NaOAc, pH 5.0. The RNA was dissolved in DEPC-treated water and stored at −70° C.

PolyA$^+$ mRNA was isolated from total RNA using the PolyA$^+$ tract mRNA Isolation System available from Promega. PolyA$^+$ mRNA was used as a template for cDNA synthesis using the ZAP Express® cDNA synthesis system available from Stratagene (La Jolla, Calif.)

Carnation Petal cDNA Library Screening

A cDNA library made using mRNA isolated from stage IV carnation petals was diluted to approximately $5 \times 10^6$ PFU/ml and immunoscreened with lipid particle antiserum. Positive cDNA clones were recovered using the ExAssist® Helper Phage/SOLR strain system and recircularized in a pBluescript® phagemid (Stratagene). A stage III carnation petal cDNA library was also screened using a $^{32}$P-labelled 19 base pair probe (5'-ACCTACTAGGTTCCGCGTC-3') (SEQ ID NO:5). Positive cDNA clones were excised from the phages and recircularized into a pBK-CMV® (Stratagene) phagemid using the method in the manufacturer's instructions. The full length cDNA (1.53 kb fragment) was inserted into the PBK-CMV vector.

*Arabidopsis* Leaf cDNA Library Screening

A full-length cDNA clone (1338 bp) of the senescence-induced lipase gene from *Arabidopsis thaliana* was isolated by screening an *Arabidopsis* senescent leaf cDNA library. The probe used for screening the library was obtained by PCR using the scenescent leaf library as template. The PCR primers were designed from the genomic sequence (U93215) present in GenBank. The forward primer had the sequence 5' ATG TCT AGA GAA GAT ATT GCG CGG CGA 3' (SEQ ID NO:20) and the reverse primer had the sequence 5' GAT GAG CTC GAC GGA GCT GAG AGA GAT G 3' (SEQ ID NO:21). The PCR product was subcloned into Bluescript for sequencing. The nucleotide and amino acid sequence of the PCR product used are shown in FIG. 14.

Plasmid DNA Isolation, DNA Sequencing

The alkaline lysis method described by Sambrook et al., (Supra) was used to isolate plasmid DNA. The full length positive cDNA clone was sequenced using the dideoxy sequencing method. Sanger, et al., Proc. Natl. Acad. Sci. USA, 74:5463–5467. The open reading frame was compiled and analyzed using BLAST search (GenBank, Bethesda, Md.) and alignment of the five most homologous proteins with the derived amino acid sequence of the encoded gene was achieved using a BCM Search Launcher: Multiple Sequence Alignments Pattern-Induced Multiple Alignment Method (See F. Corpet, Nuc. Acids Res., 16:10881–10890, (1987)). Functional motifs present in the derived amino acid sequence were identified by MultiFinder.

Expression of the Lipase as a Fusion Protein

Phagemid PBK-CMV containing the full length carnation senescence-induced lipase was digested with EcoRI and XbaI, which released the 1.53 Kb lipase fragment, which was subcloned into an EcoRI and XbaI digested fusion vector, pMalc (New England BioLabs). The pMalc vector containing the senescence-induced lipase, designated pMLip, was used to transform *E. coli* BL-21 (DE3) cells.

The fusion protein encoded by pMLip, (fusion of the senescence-induced lipase and maltose binding protein) was isolated and purified as described in Sambrook, et al. (Supra) and Ausubel, et al., in Current Protocols in Molecular Biology, Green Publishing Associates and Wiley Interscience, New York, (1987), 16.4.1–16.4.3. Briefly, *E. coli* BL-21 cells transformed with pMLip were resuspended in 3 ml/g lysate buffer (50 mM Tris, pH 8.0, 100 mM NaCl and 1 mM EDTA) containing 8 μl of 50 mM PMSF and 80 μl of 20 mg/ml lysozyme per gram of cells and incubated for twenty minutes at room temperature with shaking. Then, 80 μl of 5% deoxycholic acid and 40 units of DNAse I were added and the cells were shaken at room temperature until the cells completely lysed. The cell debris was pelleted by centrifugation and resuspended in two volumes of lysate buffer plus 8 M urea and 0.1 mM PMSF. After one hour, seven volumes of buffer (50 mM $KH_2PO_4$, 1 mM EDTA and 50 mM NaCl, pH 7.0) were added to neutralize the suspension. The pH of the cell suspension was adjusted to pH 8.0 with HCl and the cell debris was pelleted. The supernatant was dialyzed against 20 mM Tris buffer, pH 8.0, 100 mM NaCl and 1 mM EDTA at 4° C. overnight. The maltose binding protein-lipase fusion product (Malip) was purified using an amylose column (available from New England BioLab). Fractions containing the fusion protein were cleaved with Protease Factor Xa (1 μg/100 μg fusion protein) to separate lipase from the fusion product. Both the fusion protein and the cleaved lipase were analyzed by SDS PAGE electrophoresis and Western blots. Maltose binding protein encoded by pMalc was used as a control. The results are shown in FIG. 3.

Northern Blot Hybridizations of Carnation RNA

Ten μg of total RNA isolated from flowers at stages I, II, III, IV were separated on 1% denatured formaldehyde agarose gels and immobilized on nylon membranes. The 1.53 Kb EcoRI-XbaI lipase fragment labelled with $^{32}$P-dCTP using a random primer kit (Boehringer Mannheim) was used to probe the filters ($7 \times 10^7$ cpm). The filters were washed once with 1×SSC, 0.1% SDS at room temperature and three times with 0.2×SSC, 0.1% SDS at 65° C. The filters were dried and exposed to X-ray film overnight at −70° C. The results are shown in FIG. 4.

Northern Blot Hybridization of *Arabidopsis* RNA

Ten μg of total RNA isolated from *Arabidopsis* leaves at weeks 2, 3, 4, 5 and 6 of growth were separated on 1% denatured formaldehyde agarose gels and immobilized on nylon membranes. The full-length *Arabidopsis* senescence-induced lipase gene labelled with $^{32}$P-dCTP using a random primer kit (Boehringer Mannheim) was used to probe the filters ($7 \times 10^7$ cpm). The filters were washed once with 1×SSC, 0.1% SDS at room temperature and three times with 0.2×SSC, 0.1% SDS at 65° C. The filters were dried and exposed to X-ray film overnight at −70° C.

Genomic DNA Isolation And Southern Blot Hybridizations

Freshly cut carnation petals were frozen in liquid nitrogen, ground to a powder and homogenized (2 ml/g) with extraction buffer (0.1 M Tris, pH 8.2, 50 mM EDTA, 0.1M NaCl, 2% SDS, and 0.1 mg/ml proteinase K) to isolate genomic DNA. The homogenized material was incubated at 37° C. for ten minutes and extracted with phenol-chloroform-isoamyl alcohol (25:24:1). DNA was precipitated with NaOAc and isopropanol. The DNA pellet was dissolved in 1×TE, pH 8.0, re-extracted with phenol, reprecipitated and resuspended in 1×TE, pH 8.0.

Genomic DNA was digested with restriction endonucleases (Bam HI, XbaI, XhoI, EcoRI, HindIII and SalI) separately and the digested DNA was fractionated on a 1% agarose gel. The separated DNA was blotted onto nylon membranes and hybridizations were carried out using $^{32}$P-dCTP-labelled 1.53 Kb lipase fragment. Hybridization and washing were carried out under high stringency conditions (68° C.))6×SSC, 2× Denhardt's reagent, 0.1% SDS) as well as low stringency conditions (42° C. for hybridization and washing) (6×SSC, 5× Denhardt's reagent, 0.1% SDS). The results are shown in FIG. 6. As can be seen, the lipase cDNA probe detects only one genomic fragment, indicating that the carnation lipase gene is a single copy gene.

Lipase Enzyme Assays

Lipolytic acyl hydrolase activity of the purified lipase fusion protein was assayed spectrophotometrically using p-nitrophenylpalmitate and soybean phospholipid as exogenous substrates. For maltose-binding protein alone, which served as a control, there was no detectable lipase activity with phospholipid as a substrate (Table 2). When p-nitrophenylpalmitate was used as a substrate with maltose-binding protein alone, a small amount of p-nitrophenol, the expected product of a lipase reaction, was detectable reflecting background levels of p-nitrophenol in the commercial preparation of p-nitrophenylpalmitate (Table 2). However, in the presence of purified lipase fusion protein, strong lipase activity manifested as the release of free fatty acids from phospholipid and p-nitrophenol from p-nitrophenylpalmitate was evident (Table 2).

TABLE 2

Spectrophotometric measurements of the lipolytic acyl hydrolase activity of maltose-binding protein and lipase fusion protein expressed in E. coil and purified by amylose column chromatography.
Two substrates, p-nitrophenylpalmitate and soybean phospholipid, were used.
Activities are expressed in terms of product formed (p-nitrophenol from p-nitrophenylpalmitate and free fatty acid from soybean phospholipid).
Means ± SE for n = 3 replications are shown.

| | PRODUCT | |
|---|---|---|
| Protein Species | pNPP p-nitrophenol (nmol/mg/min) | free fatty acid (nmol/mg protein/min) |
| Maltose-binding protein | 0.71 ± 0.02 | ND* |
| Lipase fusion protein | 12.01 ± 1.81 | 46.75 ± 1.24 |

*ND, not detectable

In other experiments, the enzymatic activity of the lipase fusion protein was assayed by gas chromatography, a technique that enables quantitation and identification of free fatty acids released from the substrate. Trilinolein, soybean phospholipid and dilinoleylphosphatidylcholine were used as substrates, and the deesterified fatty acids were purified by thin layer chromatography prior to being analyzed by gas chromatography. In keeping with the spectrophotometric assay (Table 2), there was no detectable lipase activity for maltose-binding protein alone with either soybean phospholipid or dilinoleylphosphatidylcholine, indicating that these substrates are essentially free of deesterified fatty acids (Table 3). However, when the lipase fusion protein was used as a source of enzyme, palmitic, stearic and linoleic acids were deesterified from the soybean phospholipid extract, and linoleic acid was deesterified from dilinoleylphosphatidylcholine (Table 3). In contrast to the phospholipid substrates, detectable levels of free linoleic acid were present in trilinolein, but the levels of free linoleic acid were significantly increased in the presence of lipase fusion protein indicating that the lipase is capable of deesterifying fatty acids from triacylglycerol as well (Table 3).

TABLE 3

GC measurements of the lipolytic acyl hydrolase activity of maltose-binding protein and lipase fusion protein expressed in E. coli and purified by amylose column chromatography

| | | Products (μg/mg protein)[1] | |
|---|---|---|---|
| Substrates | | Maltose-binding Protein | Lipase fusion Protein |
| Tri-linolein[2] | Linoleic acid (18:2) | 15.9 ± 0.75 | 33.4 ± 1.58 |
| Soybean phospholipids[3] | Palmitic acid (16:0) | ND[4] | 4.80 |
| | Stearic acid (18:0) | ND | 9.68 |
| | Linoleic acid (18:2) | ND | 5.80 |
| Dilinoleylphos-phatydilcholine[3] | Linoleic acid (18:2) | ND | 20.0 |

[1] Reaction was allowed to proceed for 2 hours, and was not continuously linear over this period.
[2] Means ± SE for n = 3 replications are shown
[3] Single experiment
[4] Not detectable Lipase activity of the protein obtained by expression of the lipase cDNA in E. coli was measured in vivo as described in Tsuboi, et al., Infect. Immunol., 64:2936–2940 (1996); Wang, et al., Biotech., 9:741–746 (1995); and G. Sierra, J. Microbiol. and Serol., 23:15–22 (1957). A single colony of E. coli BL-21 cells transformed with pMal and another E. coli BL-21 colony transformed with pMLip were inoculated in basal salt medium (pH 7.0) containing (g/L): $K_2HPO_4$ (4.3), $KH_2PO_4$ (3.4), $(NH_4)SO_4$ (2.0), $MgCl_2$ (0.16), $MnCl_2.4H_2O$ (0.001), $FeSO_4.7H_2O$ (0.0006), $CaCl_2.2H_2O$ (0.026), and $NaMoO_4.2H_2O$ (0.002). Substrate, Tween 40 (polyoxyethylenesorbitan monopalmitate) or Tween 60 (polyoxyethylenesorbitan monostearate), was added at a concentration of 1%. Growth of the bacterial cells at 37° C. with shaking was monitored by measuring the absorbance at 600 nm (FIG. 5). As can be seen in FIG. 5, E. coli cells transformed with pMLip were capable of growth in the Tween40/Tween60-supplemented basal medium, after an initial lag period. However, E. coli cells transformed with pMal did not grow in the Tween-supplemented medium.

EXAMPLE 2

Ethylene Induction of Carnation Senescence-Induced Lipase Gene

Stage II carnation flowers and carnation cuttings were treated with 0.5 ppm ethylene in a sealed chamber for 15 hours. RNA was extracted from the ethylene treated Stage II flower petals and from leaves of the treated cutting, as well as from the flower and leaves of untreated carnation flowers and cuttings as described below.

Arabidopsis plants were treated with 50 μM ethephon in a sealed chamber for one, two or three days. RNA was extracted from the ethephon treated leaves of the plants as follows.

Flowers or leaves (1 flower or 5 g leaves) were ground in liquid nitrogen. The ground powder was mixed with 30 ml guanidinium buffer (4 M guanidinium isothiocyanate, 2.5 mM NaOAc pH 8.5, 0.8% β-mercaptoethanol). The mixture was filtered through four layers of cheesecloth and centrifuged at 10,000 g at 4° C. for 30 minutes. The supernatant was then subjected to cesium chloride density gradient centrifugation at 26,000 g for 20 hours. The pelleted RNA was rinsed with 75% ethanol, resuspended in 600 μl DEPC-treated water and the RNA precipitated at −70° C. with 0.75 ml 95% ethanol and 30 μl of 3M NaOAc. Ten μg of either carnation or Arabidopsis RNA were fractionated on a 1.2% denaturing formaldehyde agarose gel and transferred to a nylon membrane. Randomly primed [32]P-dCTP-labelled full length carnation lipase cDNA (SEQ ID NO:1) was used to probe the membrane containing carnation RNA at 42° C. overnight. Randomly primed [32]P-dCTP-labelled full length Arabidopsis lipase cDNA was used to probe the membrane containing Arabidopsis RNA at 42° C. overnight. The membranes were then washed once in 1×SSC containing 0.1% SDS at room temperature for 15 minutes and three times in 0.2×SSC containing 0.1% SDS at 65° C. for 15 minutes each. The membranes were exposed to x-ray film overnight at −70° C.

Figure 9A:
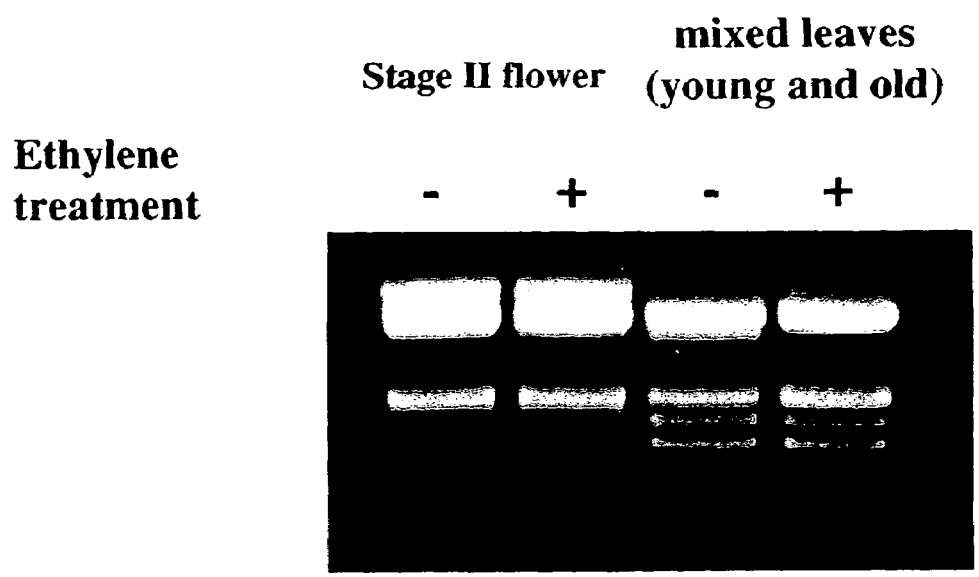
FIG. 9A is a Northern blot analysis showing the expression of the carnation lipase in stage II petals that have been exposed to 0.5 ppm ethylene for 15 hours.
Figure 9B:
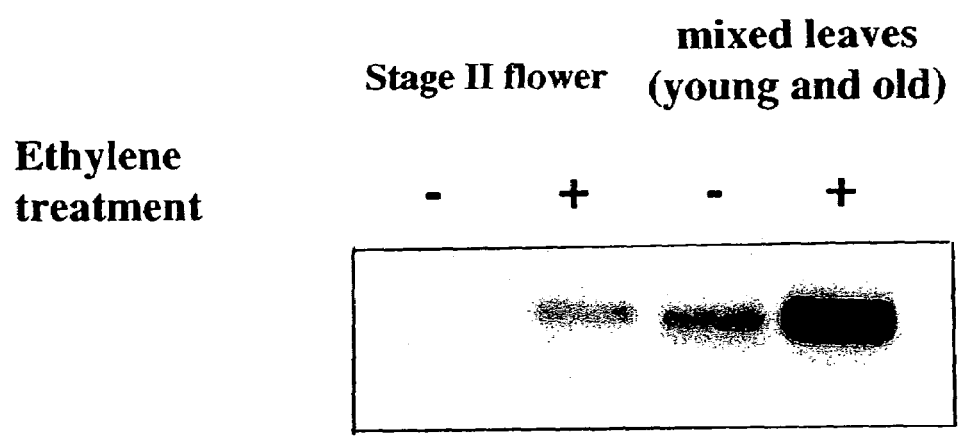
FIG. 9B is an autoradiogram of a Northern blot of the gel in FIG. 9A probed with labelled full length carnation petal senescence-induced lipase cDNA.

The results are shown in FIG. 9 (carnation) and FIG. 16 (Arabidopsis; lane 1, one day treatment; lane 2, two days treatment; lane 3, three days treatment). As can be seen, transcription of the carnation lipase and Arabidopsis lipase is induced in flowers and/or leaves by ethylene.

EXAMPLE 3

Generation of Tomato PCR Product Using Carnation Lipase Primers

A partial length senescence-induced lipase sequence from tomato genomic DNA obtained from tomato leaves was generated by nested PCR using a pair of oligonucleotide primers designed from carnation senescence-induced lipase sequence. The 5' primer is a 19-mer having the sequence, 5'-CTCTAGACTATGAGTGGGT (SEQ ID NO:7); the 3' primer is an 18-mer having the sequence, CGACTGGCA-CAACCTCCA-3' (SEQ ID NO:8). Polymerase chain reaction, using genomic tomato DNA was carried out as follows:

Reaction Components:

| | |
|---|---|
| Genomic DNA | 100 ng |
| dNTP (10 mM each) | 1 µl |
| MgCl$_2$ (5 mM) + 10 × buffer | 5 µl |
| Primers 1 and 2 (20 µM each) | 0.5 µl |
| Taq DNA polymerase | 1.25 U |
| Reaction volume | 50 µl |

Reaction Parameters:
94° C. for 3 min 94° C./1 min, 48° C./1 min, 72° C./2 min, for 45 cycles 72° C. for 15 min.

Figure 10:
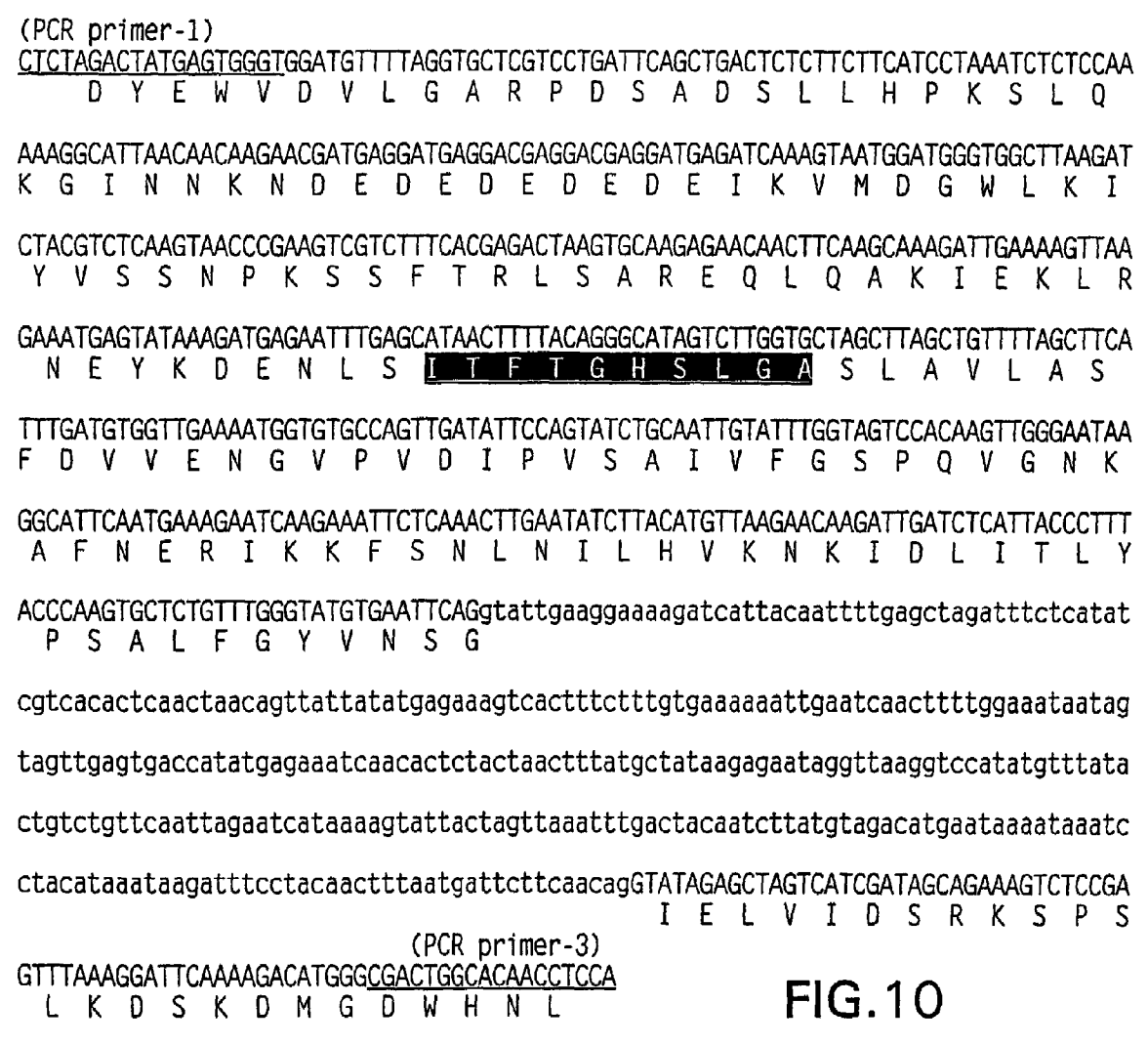

The tomato partial length sequence obtained by PCR has the nucleotide sequence, SEQ ID NO:6 (FIG. 10) and a deduced amino acid sequence as set forth in FIG. 10. The partial length sequence contains an intron (FIG. 10, lower case letters) interspersed between two coding sequences. The tomato sequence contains the conserved lipase consensus sequence, ITFTGHSLGA (SEQ ID NO:3).

The tomato sequence has 53.4% sequence identity with the carnation senescence-induced lipase sequence and 43.5% sequence identity with Arabidopsis lipase, the latter of which has 44.3% sequence identity with the carnation sequence.

EXAMPLE 4

Effect of Chilling on Cell Membrane Integrity in Tomato Plants

Tomato plants were chilled for 48 hours at 7° C. to 8° C. and then returned to room temperature for 24 hours. The effect of chilling on leaves was assessed by measuring the amount of electrolyte leakage (µMhos).

Specifically, 1 g of leaf tissue was cut into a 50 ml tube, quick-rinsed with distilled water, and 40 ml of deionized water added. The tubes were capped and rotated at room temperature for 24 hours. Conductivity (µMho) readings reflecting electrolyte leakage were taken at 6 and 24 hour intervals for control and chill-injured leaf tissue. It is clear from FIG. 11 that electrolyte leakage reflecting membrane damage is incurred during the rewarming period in chill injured leaf tissue.

Northern Blot Analysis of RNA Obtained from Chilled Tomato Leaves

Total RNA was isolated from the leaves 15 g of unchilled tomato plants (control) and chilled tomato plants that had been returned to room temperature for 0, 6 and 24 hours. RNA extraction was carried out as described in Example 3. 10 µg of RNA from each sample was separated on a 1.2% denaturing formaldehyde gel and transferred to a nylon membrane. The membrane was probed with $^{32}$P-dCTP-labelled probe (SEQ ID NO:3) and then washed under the same conditions as described in Example 3. The results are shown in FIG. 12.

As can be seen from the autoradiograph (FIG. 12B) tomato lipase gene expression is induced by chilling and the pattern of gene induction correlates with increased electrolyte leakage in chill injured leaves (FIG. 11).

EXAMPLE 5

Generation of Transgenic Plants Expressing Senescence-Induced Lipase Gene in Antisense Orientation Agrobacteria were transformed with the binary vector, pKYLX71, containing the full-length Arabidopsis senescence-induced lipase gene expressed in antisense orientation under the regulation of double 35S promoter. Arabidopsis plants were transformed with these Agrobacteria by vacuum filtration, and transformed seeds from the resultant T$_0$ plants were selected on ampicillin.

T$_1$ plants were grown under greenhouse conditions, alongside wild-type Arabidopsis plants. Differences in leaf size, overall plant size, seed yield and leaf senescence between transgenic and wild-type plants were observed over time. Differences are illustrated in FIGS. 17, 18, 19, and 20.

EXAMPLE 6

Reduced Senescence-Induced Lipase Production in Transgenic Plants

Total protein isolated from leaves of four week-old Arabidopsis wild-type and corresponding transgenic plants made as in example 5 was transferred to a nylon membrane and probed with antibody raised against the Arabidopsis senescence-induced lipase protein. The Western blot is shown in FIG. 21. (Lanes 1 and 2 were loaded with 9 µg of protein, and lanes 3 and 4 were loaded with 18 µg of protein). The expression of the senescence-induced lipase was reduced in transgenic plants.

What is claimed is:

1. An isolated senescence-induced lipase encoded by a nucleotide sequence which has at least 90% sequence identity to SEQ ID NO: 1, and wherein the nucleotide sequence encodes an amino acid sequence that has senescence-induced lipase activity of SEQ ID NO: 2.

2. The senescence-induced lipase of claim 1 wherein the lipase has the amino acid sequence SEQ ID NO: 2.

* * * * *

SEQUENCE LISTING

<160> NUMBER OF SEQ ID NOS: 21

<210> SEQ ID NO 1
<211> LENGTH: 1537
<212> TYPE: DNA
<213> ORGANISM: Plant
<220> FEATURE:
<221> NAME/KEY: CDS
<222> LOCATION: (48)...(1390)

<400> SEQUENCE: 1

-continued

| | |
|---|---|
| gcacgagcca ttccaaaact ccttacacca ctcaaaacta ttccaac atg gct gca<br>                                                                                        Met Ala Ala<br>                                                                                         1 | 56 |
| gaa gcc caa cct tta ggc ctc tca aag ccc ggc cca aca tgg ccc gaa<br>Glu Ala Gln Pro Leu Gly Leu Ser Lys Pro Gly Pro Thr Trp Pro Glu<br> 5                         10                        15 | 104 |
| ctc ctc ggg tcc aat gct tgg gcc ggg cta cta aac ccg ctc aac gat<br>Leu Leu Gly Ser Asn Ala Trp Ala Gly Leu Leu Asn Pro Leu Asn Asp<br>  20                       25                   30                        35 | 152 |
| gag ctc cgt gag ctc ctc cta cgc tgc ggg gac ttc tgc cag gtg aca<br>Glu Leu Arg Glu Leu Leu Leu Arg Cys Gly Asp Phe Cys Gln Val Thr<br>          40                        45                        50 | 200 |
| tac gac acc ttc ata aac gac cag aac tcg tcc tac tgc ggc agc agc<br>Tyr Asp Thr Phe Ile Asn Asp Gln Asn Ser Ser Tyr Cys Gly Ser Ser<br>              55                        60                        65 | 248 |
| cgc tac ggg aag gcg gac cta ctt cat aag acc gcc ttc ccg ggg ggc<br>Arg Tyr Gly Lys Ala Asp Leu Leu His Lys Thr Ala Phe Pro Gly Gly<br>        70                        75                        80 | 296 |
| gca gac cgg ttt gac gtg gtg gcg tac ttg tac gcc act gcg aag gtc<br>Ala Asp Arg Phe Asp Val Val Ala Tyr Leu Tyr Ala Thr Ala Lys Val<br>85                        90                        95 | 344 |
| agc gtc cca gag gcg ttt ctg ctg aag tcg agg tcg agg gag aag tgg<br>Ser Val Pro Glu Ala Phe Leu Leu Lys Ser Arg Ser Arg Glu Lys Trp<br>100                     105                   110                  115 | 392 |
| gat agg gaa tcg aat tgg att ggg tat gtc gtg gtg tcg aat gac gag<br>Asp Arg Glu Ser Asn Trp Ile Gly Tyr Val Val Val Ser Asn Asp Glu<br>                    120                   125                   130 | 440 |
| acg agt cgg gtg gcg gga cga agg gag gtg tat gtg gtg tgg aga ggg<br>Thr Ser Arg Val Ala Gly Arg Arg Glu Val Tyr Val Val Trp Arg Gly<br>              135                   140                   145 | 488 |
| act tgt agg gat tat gag tgg gtt gat gtt ctt ggt gct caa ctt gag<br>Thr Cys Arg Asp Tyr Glu Trp Val Asp Val Leu Gly Ala Gln Leu Glu<br>        150                       155                   160 | 536 |
| tct gct cat cct ttg tta cgc act caa caa act act cat gtt gaa aag<br>Ser Ala His Pro Leu Leu Arg Thr Gln Gln Thr Thr His Val Glu Lys<br>165                     170                   175 | 584 |
| gtg gaa aat gag gaa aag aag agc att cat aaa tca agt tgg tac gac<br>Val Glu Asn Glu Glu Lys Lys Ser Ile His Lys Ser Ser Trp Tyr Asp<br>180                     185                   190                  195 | 632 |
| tgt ttc aat atc aac cta cta ggt tcc gcg tcc aaa gac aaa gga aaa<br>Cys Phe Asn Ile Asn Leu Leu Gly Ser Ala Ser Lys Asp Lys Gly Lys<br>                  200                   205                   210 | 680 |
| gga agc gac gac gac gat gat gac gac ccc aaa gtg atg caa ggt tgg<br>Gly Ser Asp Asp Asp Asp Asp Asp Pro Lys Val Met Gln Gly Trp<br>             215                   220                   225 | 728 |
| atg aca ata tac aca tcg gag gat ccc aaa tca ccc ttc aca aaa cta<br>Met Thr Ile Tyr Thr Ser Glu Asp Pro Lys Ser Pro Phe Thr Lys Leu<br>        230                       235                   240 | 776 |
| agt gca aga aca caa ctt cag acc aaa ctc aaa caa cta atg aca aaa<br>Ser Ala Arg Thr Gln Leu Gln Thr Lys Leu Lys Gln Leu Met Thr Lys<br>245                     250                   255 | 824 |
| tac aaa gac gaa acc cta agc ata aca ttc gcc ggt cac agc cta ggc<br>Tyr Lys Asp Glu Thr Leu Ser Ile Thr Phe Ala Gly His Ser Leu Gly<br>260                     265                   270                  275 | 872 |
| gcg aca cta tca gtc gtg agc gcc ttc gac ata gtg gag aat ctc acg<br>Ala Thr Leu Ser Val Val Ser Ala Phe Asp Ile Val Glu Asn Leu Thr<br>              280                   285                   290 | 920 |
| acc gag atc cca gtc acg gcc gtg gtc ttc ggg tgc cca aaa gta ggc<br>Thr Glu Ile Pro Val Thr Ala Val Val Phe Gly Cys Pro Lys Val Gly | 968 |

```
                    295                 300                 305
aac aaa aaa ttc caa caa ctc ttc gac tcg tac cca aac cta aat gtc     1016
Asn Lys Lys Phe Gln Gln Leu Phe Asp Ser Tyr Pro Asn Leu Asn Val
            310                 315                 320 ctc cat gta agg aat gtc atc gac ctg atc cct ctg tat ccc gtg aaa     1064
Leu His Val Arg Asn Val Ile Asp Leu Ile Pro Leu Tyr Pro Val Lys
        325                 330                 335 ctc atg ggt tac gtg aac ata gga atc gag ctg gag atc gac tcg agg     1112
Leu Met Gly Tyr Val Asn Ile Gly Ile Glu Leu Glu Ile Asp Ser Arg
340                 345                 350                 355 aag tcg acc ttt cta aag gac tcg aaa aac ccg agt gat tgg cat aat     1160
Lys Ser Thr Phe Leu Lys Asp Ser Lys Asn Pro Ser Asp Trp His Asn
                360                 365                 370 ttg caa gca ata ttg cat gtt gta agt ggt tgg cat ggg gtt aag ggg     1208
Leu Gln Ala Ile Leu His Val Val Ser Gly Trp His Gly Val Lys Gly
            375                 380                 385 gag ttt aag gtt gta aat aag aga agt gtt gca ttg gtt aat aag tca     1256
Glu Phe Lys Val Val Asn Lys Arg Ser Val Ala Leu Val Asn Lys Ser
        390                 395                 400 tgt gat ttt ctt aag gaa gaa tgt ttg gtt cct cca gct tgg tgg gtt     1304
Cys Asp Phe Leu Lys Glu Glu Cys Leu Val Pro Pro Ala Trp Trp Val
405                 410                 415 gtg cag aac aaa ggg atg gtt ttg aat aag gat ggt gag tgg gtt ttg     1352
Val Gln Asn Lys Gly Met Val Leu Asn Lys Asp Gly Glu Trp Val Leu
420                 425                 430                 435 gct cct cct gag gaa gat cct act cct gaa ttt gat tg ataatatttc       1400
Ala Pro Pro Glu Glu Asp Pro Thr Pro Glu Phe Asp
                440                 445 atcatgttttt atatttttat aaatttact aaatttacat gacaatttat gggactaagt   1460
tacttattta tatgtttatt atatttgaaa tgtgttttaa gttacataaa attgcaatta   1520
gttttaaaaa aaaaaaa                                                  1537

<210> SEQ ID NO 2
<211> LENGTH: 447
<212> TYPE: PRT
<213> ORGANISM: Plant

<400> SEQUENCE: 2

Met Ala Ala Glu Ala Gln Pro Leu Gly Leu Ser Lys Pro Gly Pro Thr
1               5                   10                  15

Trp Pro Glu Leu Leu Gly Ser Asn Ala Trp Ala Gly Leu Leu Asn Pro
            20                  25                  30

Leu Asn Asp Glu Leu Arg Glu Leu Leu Arg Cys Gly Asp Phe Cys
        35                  40                  45

Gln Val Thr Tyr Asp Thr Phe Ile Asn Asp Gln Asn Ser Ser Tyr Cys
    50                  55                  60

Gly Ser Ser Arg Tyr Gly Lys Ala Asp Leu Leu His Lys Thr Ala Phe
65                  70                  75                  80

Pro Gly Gly Ala Asp Arg Phe Asp Val Val Ala Tyr Leu Tyr Ala Thr
                85                  90                  95

Ala Lys Val Ser Val Pro Glu Ala Phe Leu Leu Lys Ser Arg Ser Arg
            100                 105                 110

Glu Lys Trp Asp Arg Glu Ser Asn Trp Ile Gly Tyr Val Val Ser
        115                 120                 125

Asn Asp Glu Thr Ser Arg Val Ala Gly Arg Arg Glu Val Tyr Val Val
    130                 135                 140
```

-continued

```
Trp Arg Gly Thr Cys Arg Asp Tyr Glu Trp Val Asp Val Leu Gly Ala
145                 150                 155                 160

Gln Leu Glu Ser Ala His Pro Leu Leu Arg Thr Gln Gln Thr Thr His
            165                 170                 175

Val Glu Lys Val Glu Asn Glu Lys Lys Ser Ile His Lys Ser Ser
        180                 185                 190

Trp Tyr Asp Cys Phe Asn Ile Asn Leu Leu Gly Ser Ala Ser Lys Asp
        195                 200                 205

Lys Gly Lys Gly Ser Asp Asp Asp Asp Asp Pro Lys Val Met
        210                 215                 220

Gln Gly Trp Met Thr Ile Tyr Thr Ser Glu Asp Pro Lys Ser Pro Phe
225                 230                 235                 240

Thr Lys Leu Ser Ala Arg Thr Gln Leu Gln Thr Lys Leu Lys Gln Leu
            245                 250                 255

Met Thr Lys Tyr Lys Asp Glu Thr Leu Ser Ile Thr Phe Ala Gly His
            260                 265                 270

Ser Leu Gly Ala Thr Leu Ser Val Val Ser Ala Phe Asp Ile Val Glu
        275                 280                 285

Asn Leu Thr Thr Glu Ile Pro Val Thr Ala Val Val Phe Gly Cys Pro
        290                 295                 300

Lys Val Gly Asn Lys Lys Phe Gln Gln Leu Phe Asp Ser Tyr Pro Asn
305                 310                 315                 320

Leu Asn Val Leu His Val Arg Asn Val Ile Asp Leu Ile Pro Leu Tyr
                325                 330                 335

Pro Val Lys Leu Met Gly Tyr Val Asn Ile Gly Ile Glu Leu Glu Ile
            340                 345                 350

Asp Ser Arg Lys Ser Thr Phe Leu Lys Asp Ser Lys Asn Pro Ser Asp
            355                 360                 365

Trp His Asn Leu Gln Ala Ile Leu His Val Val Ser Gly Trp His Gly
        370                 375                 380

Val Lys Gly Glu Phe Lys Val Val Asn Lys Arg Ser Val Ala Leu Val
385                 390                 395                 400

Asn Lys Ser Cys Asp Phe Leu Lys Glu Glu Cys Leu Val Pro Pro Ala
                405                 410                 415

Trp Trp Val Val Gln Asn Lys Gly Met Val Leu Asn Lys Asp Gly Glu
            420                 425                 430

Trp Val Leu Ala Pro Pro Glu Glu Asp Pro Thr Pro Glu Phe Asp
            435                 440                 445
```

<210> SEQ ID NO 3
<211> LENGTH: 10
<212> TYPE: PRT
<213> ORGANISM: Plant

<400> SEQUENCE: 3

```
Ile Thr Phe Thr Gly His Ser Leu Gly Ala
1               5                   10
```

<210> SEQ ID NO 4
<211> LENGTH: 10
<212> TYPE: PRT
<213> ORGANISM: Plant

<400> SEQUENCE: 4

```
Ile Thr Phe Ala Gly His Ser Leu Gly Ala
1               5                   10
```

```
<210> SEQ ID NO 5
<211> LENGTH: 19
<212> TYPE: DNA
<213> ORGANISM: Plant

<400> SEQUENCE: 5
acctactagg ttccgcgtc                                                   19

<210> SEQ ID NO 6
<211> LENGTH: 923
<212> TYPE: DNA
<213> ORGANISM: Plant
<220> FEATURE:
<221> NAME/KEY: CDS
<222> LOCATION: (6)...(512)
<220> FEATURE:
<221> NAME/KEY: intron
<222> LOCATION: (513)...(843)
<220> FEATURE:
<221> NAME/KEY: CDS
<222> LOCATION: (844)...(921)

<400> SEQUENCE: 6 ctcta gac tat gag tgg gtg gat gtt tta ggt gct cgt cct gat tca gct       50
      Asp Tyr Glu Trp Val Asp Val Leu Gly Ala Arg Pro Asp Ser Ala
        1               5                  10                  15 gac tct ctt ctt cat cct aaa tct ctc caa aaa ggc att aac aac aag         98
Asp Ser Leu Leu His Pro Lys Ser Leu Gln Lys Gly Ile Asn Asn Lys
         20                  25                  30 aac gat gag gat gag gac gag gac gag gat gag atc aaa gta atg gat        146
Asn Asp Glu Asp Glu Asp Glu Asp Glu Asp Glu Ile Lys Val Met Asp
 35                  40                  45 ggg tgg ctt aag atc tac gtc tca agt aac ccg aag tcg tct ttc acg        194
Gly Trp Leu Lys Ile Tyr Val Ser Ser Asn Pro Lys Ser Ser Phe Thr
         50                  55                  60 aga cta agt gca aga gaa caa ctt caa gca aag att gaa aag tta aga        242
Arg Leu Ser Ala Arg Glu Gln Leu Gln Ala Lys Ile Glu Lys Leu Arg
 65                  70                  75 aat gag tat aaa gat gag aat ttg agc ata act ttt aca ggg cat agt        290
Asn Glu Tyr Lys Asp Glu Asn Leu Ser Ile Thr Phe Thr Gly His Ser
 80                  85                  90                  95 ctt ggt gct agc tta gct gtt tta gct tca ttt gat gtg gtt gaa aat        338
Leu Gly Ala Ser Leu Ala Val Leu Ala Ser Phe Asp Val Val Glu Asn
             100                 105                 110 ggt gtg cca gtt gat att cca gta tct gca att gta ttt ggt agt cca        386
Gly Val Pro Val Asp Ile Pro Val Ser Ala Ile Val Phe Gly Ser Pro
         115                 120                 125 caa gtt ggg aat aag gca ttc aat gaa aga atc aag aaa ttc tca aac        434
Gln Val Gly Asn Lys Ala Phe Asn Glu Arg Ile Lys Lys Phe Ser Asn
 130                 135                 140 ttg aat atc tta cat gtt aag aac aag att gat ctc att acc ctt tac        482
Leu Asn Ile Leu His Val Lys Asn Lys Ile Asp Leu Ile Thr Leu Tyr
         145                 150                 155 cca agt gct ctg ttt ggg tat gtg aat tca ggtattgaag gaaaagatca          532
Pro Ser Ala Leu Phe Gly Tyr Val Asn Ser
160                 165 ttacaatttt gagctagatt tctcatatcg tcacactcaa ctaacagtta ttatatgaga      592
aagtcacttt ctttgtgaaa aaattgaatc aactttttgga aataatagta gttgagtgac     652
catatgagaa atcaacactc tactaacttt atgctataag agaataggtt aaggtccata      712
tgtttatact gtctgttcaa ttagaatcat aaaagtatta ctagttaaat ttgactacaa      772
```

```
tcttatgtag acatgaataa aataaatcct acataaataa gatttcctac aactttaatg      832
attcttcaac a ggt ata gag cta gtc atc gat agc aga aag tct ccg agt       882
            Gly Ile Glu Leu Val Ile Asp Ser Arg Lys Ser Pro Ser
                170             175             180 tta aag gat tca aaa gac atg ggc gac tgg cac aac ctc ca                 923
Leu Lys Asp Ser Lys Asp Met Gly Asp Trp His Asn Leu
        185             190             195

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
ctctagacta tgagtgggt                                                    19

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
cgactggcac aacctcca                                                     18

<210> SEQ ID NO 9
<211> LENGTH: 10
<212> TYPE: PRT
<213> ORGANISM: Plant

<400> SEQUENCE: 9

Ile Thr Thr Cys Gly His Ser Leu Gly Ala
 1               5                  10

<210> SEQ ID NO 10
<211> LENGTH: 10
<212> TYPE: PRT
<213> ORGANISM: Plant

<400> SEQUENCE: 10

Ile Thr Val Thr Gly His Ser Leu Gly Ser
 1               5                  10

<210> SEQ ID NO 11
<211> LENGTH: 447
<212> TYPE: PRT
<213> ORGANISM: Plant

<400> SEQUENCE: 11

Met Ala Ala Glu Ala Gln Pro Leu Gly Leu Ser Lys Pro Gly Pro Thr
 1               5                  10                  15

Trp Pro Glu Leu Leu Gly Ser Asn Ala Trp Ala Gly Leu Leu Asn Pro
            20                  25                  30

Leu Asn Asp Glu Leu Arg Glu Leu Leu Arg Cys Gly Asp Phe Cys
        35                  40                  45

Gln Val Thr Tyr Asp Thr Phe Ile Asn Asp Gln Asn Ser Ser Tyr Cys
    50                  55                  60

Gly Ser Ser Arg Tyr Gly Lys Ala Asp Leu Leu His Lys Thr Ala Phe
65                  70                  75                  80
```

-continued

```
Pro Gly Gly Ala Asp Arg Phe Asp Val Val Ala Tyr Leu Tyr Ala Thr
                85                  90                  95

Ala Lys Val Ser Val Pro Glu Ala Phe Leu Lys Ser Arg Ser Arg
            100                 105                 110

Glu Lys Trp Asp Arg Glu Ser Asn Trp Ile Gly Tyr Val Val Ser
        115                 120                 125

Asn Asp Glu Thr Ser Arg Val Ala Gly Arg Arg Glu Val Tyr Val Val
    130                 135                 140

Trp Arg Gly Thr Cys Arg Asp Tyr Glu Trp Val Asp Val Leu Gly Ala
145                 150                 155                 160

Gln Leu Glu Ser Ala His Pro Leu Leu Arg Thr Gln Thr Thr His
            165                 170                 175

Val Glu Lys Val Glu Asn Glu Lys Lys Ser Ile His Lys Ser Ser
            180                 185                 190

Trp Tyr Asp Cys Phe Asn Ile Asn Leu Leu Gly Ser Ala Ser Lys Asp
        195                 200                 205

Lys Gly Lys Gly Ser Asp Asp Asp Asp Asp Pro Lys Val Met
    210                 215                 220

Gln Gly Trp Met Thr Ile Tyr Thr Ser Glu Asp Pro Lys Ser Pro Phe
225                 230                 235                 240

Thr Lys Leu Ser Ala Arg Thr Gln Leu Gln Thr Lys Leu Lys Cys Leu
            245                 250                 255

Met Thr Lys Tyr Lys Asp Glu Thr Leu Ser Ile Thr Phe Ala Gly His
            260                 265                 270

Ser Leu Gly Ala Thr Leu Ser Val Val Ser Ala Phe Asp Ile Val Glu
        275                 280                 285

Asn Leu Thr Thr Glu Ile Pro Val Thr Ala Val Val Phe Gly Cys Pro
    290                 295                 300

Lys Val Gly Asn Lys Lys Phe Gln Gln Leu Phe Asp Ser Tyr Pro Asn
305                 310                 315                 320

Leu Asn Val Leu His Val Arg Asn Val Ile Asp Leu Ile Pro Leu Tyr
            325                 330                 335

Pro Val Lys Leu Met Gly Tyr Val Asn Ile Gly Ile Glu Leu Glu Ile
            340                 345                 350

Asp Ser Arg Lys Ser Thr Phe Leu Lys Asp Ser Lys Asn Pro Ser Asp
        355                 360                 365

Trp His Asn Leu Gln Ala Ile Leu His Val Val Ser Gly Trp His Gly
    370                 375                 380

Val Lys Gly Glu Phe Lys Val Val Asn Lys Arg Ser Val Ala Leu Val
385                 390                 395                 400

Asn Lys Ser Cys Asp Phe Leu Lys Glu Glu Cys Leu Val Pro Pro Ala
            405                 410                 415

Trp Trp Val Val Gln Asn Lys Gly Met Val Leu Asn Lys Asp Gly Glu
            420                 425                 430

Trp Val Leu Ala Pro Pro Glu Glu Asp Pro Thr Pro Glu Phe Asp
            435                 440                 445
```

<210> SEQ ID NO 12
<211> LENGTH: 418
<212> TYPE: PRT
<213> ORGANISM: Plant

<400> SEQUENCE: 12

```
Met Lys Arg Lys Lys Lys Glu Glu Glu Glu Lys Leu Ile Val Thr
1               5                   10                  15
```

-continued

Arg Glu Phe Ala Lys Arg Trp Arg Asp Leu Ser Gly Gln Asn His Trp
            20                  25                  30

Lys Gly Met Leu Gln Pro Leu Asp Gln Asp Leu Arg Glu Tyr Ile Ile
            35                  40                  45

His Tyr Gly Glu Met Ala Gln Ala Gly Tyr Asp Thr Phe Asn Ile Asn
 50                  55                  60

Thr Glu Ser Gln Phe Ala Gly Ala Ser Ile Tyr Ser Arg Lys Asp Phe
65                  70                  75                  80

Phe Ala Lys Val Gly Leu Glu Ile Ala His Pro Tyr Thr Lys Tyr Lys
                85                  90                  95

Val Thr Lys Phe Ile Tyr Ala Thr Ser Asp Ile His Val Pro Glu Ser
            100                 105                 110

Phe Leu Leu Phe Pro Ile Ser Arg Glu Gly Trp Ser Lys Glu Ser Asn
            115                 120                 125

Trp Met Gly Tyr Val Ala Val Thr Asp Asp Gln Gly Thr Ala Leu Leu
        130                 135                 140

Gly Arg Arg Asp Ile Val Val Ser Trp Arg Gly Ser Val Gln Pro Leu
145                 150                 155                 160

Glu Trp Val Glu Asp Phe Glu Phe Gly Leu Val Asn Ala Ile Lys Ile
                165                 170                 175

Phe Gly Glu Arg Asn Asp Gln Val Gln Ile His Gln Gly Trp Tyr Ser
            180                 185                 190

Ile Tyr Met Ser Gln Asp Glu Arg Ser Pro Phe Thr Lys Thr Asn Ala
        195                 200                 205

Arg Asp Gln Val Leu Arg Glu Val Gly Arg Leu Leu Glu Lys Tyr Lys
    210                 215                 220

Asp Glu Glu Val Ser Ile Thr Ile Cys Gly His Ser Leu Gly Ala Ala
225                 230                 235                 240

Leu Ala Thr Asp Ser Ala Ile Asp Ile Val Ala Asn Gly Tyr Asn Arg
                245                 250                 255

Pro Lys Ser Arg Pro Asp Lys Ser Cys Pro Val Thr Ala Phe Val Phe
            260                 265                 270

Ala Ser Pro Arg Val Gly Asp Ser Asp Phe Arg Lys Leu Phe Ser Gly
        275                 280                 285

Leu Glu Asp Ile Arg Val Leu Arg Thr Arg Asn Leu Phe Asp Val Ile
    290                 295                 300

Pro Ile Tyr Pro Pro Ile Gly Tyr Ser Glu Val Gly Asp Glu Phe Pro
305                 310                 315                 320

Ile Asp Thr Arg Lys Ser Pro Tyr Met Lys Ser Pro Gly Asn Leu Ala
                325                 330                 335

Thr Phe His Cys Leu Glu Gly Tyr Leu His Gly Val Ala Gly Thr Gln
            340                 345                 350

Gly Thr Asn Lys Ala Asp Leu Phe Arg Leu Asp Val Glu Arg Ala Ile
        355                 360                 365

Gly Leu Val Asn Lys Ser Val Asp Gly Leu Lys Asp Glu Cys Met Val
    370                 375                 380

Pro Gly Lys Trp Arg Val Leu Lys Asn Lys Gly Ala Gln Gln Asp Asp
385                 390                 395                 400

Gly Ser Trp Glu Leu Val Asp His Glu Ile Asp Asn Glu Asp Leu
                405                 410                 415

Asp Phe

<210> SEQ ID NO 13
<211> LENGTH: 401
<212> TYPE: PRT
<213> ORGANISM: Plant

<400> SEQUENCE: 13

```
Met Ser Gly Ile Ala Lys Arg Trp Lys Val Leu Gly Ser Asp Asn
1               5                   10                  15

Trp Glu Gly Leu Leu Glu Pro Leu Asp Ser Asp Leu Arg Arg Tyr Leu
                20                  25                  30

Ile His Tyr Gly Thr Met Val Ser Pro Ala Thr Asp Ser Phe Ile Asn
            35                  40                  45

Glu Ala Ala Ser Lys Asn Val Gly Leu Pro Arg Tyr Ala Arg Arg Asn
50                  55                  60

Leu Leu Ala Asn Cys Gly Leu Val Lys Gly Asn Pro Phe Lys Tyr Glu
65                  70                  75                  80

Val Thr Lys Tyr Phe Tyr Ala Pro Ser Thr Ile Pro Leu Pro Asp Glu
                85                  90                  95

Gly Tyr Asn Val Arg Ala Thr Arg Ala Asp Ala Val Leu Lys Glu Ser
                100                 105                 110

Asn Trp Asn Gly Tyr Val Ala Val Ala Thr Asp Glu Gly Lys Val Ala
            115                 120                 125

Leu Gly Arg Arg Asp Ile Leu Ile Val Trp Arg Gly Thr Ile Arg Lys
130                 135                 140

Ser Glu Trp Asn Glu Asn Leu Thr Phe Trp Phe Val Lys Ala Pro Leu
145                 150                 155                 160

Phe Phe Gly Gln Asn Ser Asp Pro Leu Val His Lys Gly Trp Tyr Asp
                165                 170                 175

Met Tyr Thr Thr Ile Asn Gln Asp Ser Gln Leu Asn Glu Lys Ser Ala
                180                 185                 190

Arg Asp Gln Ile Arg Glu Glu Val Ala Arg Leu Val Glu Leu Tyr Lys
            195                 200                 205

Asp Glu Asp Ile Ser Ile Thr Val Thr Gly His Ser Leu Gly Ser Ser
210                 215                 220

Met Ala Thr Leu Asn Ala Val Asp Leu Ala Ala Asn Pro Ile Asn Asn
225                 230                 235                 240

Asn Lys Asn Ile Leu Val Thr Ala Phe Leu Tyr Ala Ser Pro Lys Val
                245                 250                 255

Gly Asp Glu Asn Phe Lys Asn Val Ile Ser Asn Gln Asn Leu Arg
                260                 265                 270

Ala Leu Arg Ile Ser Asp Val Asn Asp Ile Val Thr Ala Val Pro Pro
            275                 280                 285

Phe Gly Trp Lys Glu Cys Asp Asn Thr Ala Ile Leu Tyr Gly Asp Val
290                 295                 300

Gly Val Gly Leu Val Ile Asp Ser Lys Lys Ser His Tyr Leu Lys Pro
305                 310                 315                 320

Asp Phe Pro Asn Leu Ser Thr His Asp Leu Met Leu Tyr Met His Ala
                325                 330                 335

Ile Asp Gly Tyr Gln Gly Ser Gln Gly Gly Phe Glu Arg Gln Glu Asp
                340                 345                 350

Phe Asp Leu Ala Lys Val Asn Lys Tyr Gly Asp Tyr Leu Lys Ala Glu
            355                 360                 365

Tyr Pro Ile Pro Ile Gly Trp Phe Asn Ile Lys Asp Lys Gly Met Gln
370                 375                 380
```

```
Gln Asp Asp Gly Asn Tyr Ile Leu Asp Asp His Glu Val Asp Lys Thr
385                 390                 395                 400

Phe

<210> SEQ ID NO 14
<211> LENGTH: 448
<212> TYPE: PRT
<213> ORGANISM: Plant

<400> SEQUENCE: 14

Met Thr Ala Glu Asp Ile Arg Arg Asp Lys Lys Thr Glu Glu Glu
1               5                   10                  15

Arg Arg Leu Arg Asp Thr Trp Arg Lys Ile Gln Gly Glu Asp Asp Trp
            20                  25                  30

Ala Gly Leu Met Asp Pro Met Asp Pro Ile Leu Arg Ser Glu Leu Ile
            35                  40                  45

Arg Tyr Gly Glu Met Ala Gln Ala Cys Tyr Asp Ala Phe Asp Phe Asp
    50                  55                  60

Pro Ala Ser Lys Tyr Cys Gly Thr Ser Arg Phe Thr Arg Leu Glu Phe
65                  70                  75                  80

Phe Asp Ser Leu Gly Met Ile Asp Ser Gly Tyr Glu Val Ala Arg Tyr
                85                  90                  95

Leu Tyr Ala Thr Ser Asn Ile Asn Leu Pro Asn Phe Phe Ser Lys Ser
            100                 105                 110

Arg Trp Ser Lys Val Trp Ser Lys Asn Ala Asn Trp Met Gly Tyr Val
        115                 120                 125

Ala Val Ser Asp Asp Glu Thr Ser Arg Asn Arg Leu Gly Arg Arg Asp
    130                 135                 140

Ile Ala Ile Ala Trp Arg Gly Thr Val Thr Lys Leu Glu Trp Ile Ala
145                 150                 155                 160

Asp Leu Lys Asp Tyr Leu Lys Pro Val Thr Glu Asn Lys Ile Arg Cys
                165                 170                 175

Pro Asp Pro Ala Val Lys Val Glu Ser Gly Phe Leu Asp Leu Tyr Thr
            180                 185                 190

Asp Lys Asp Thr Thr Cys Lys Phe Ala Arg Phe Ser Ala Arg Glu Gln
        195                 200                 205

Ile Leu Thr Glu Val Lys Arg Leu Val Glu Glu His Gly Asp Asp Asp
    210                 215                 220

Asp Ser Asp Leu Ser Ile Thr Val Thr Gly His Ser Leu Gly Gly Ala
225                 230                 235                 240

Leu Ala Ile Leu Ser Ala Tyr Asp Ile Ala Glu Met Arg Leu Asn Arg
                245                 250                 255

Ser Lys Lys Gly Lys Val Ile Pro Val Thr Ala Val Leu Thr Tyr Gly
            260                 265                 270

Gly Pro Arg Val Gly Asn Val Arg Phe Arg Glu Arg Met Glu Glu Leu
        275                 280                 285

Gly Val Lys Val Met Arg Val Asn Val His Asp Val Val Pro Lys
    290                 295                 300

Ser Pro Gly Leu Phe Leu Asn Glu Ser Arg Pro His Ala Leu Met Lys
305                 310                 315                 320

Ile Ala Glu Gly Leu Pro Trp Cys Tyr Ser His Val Gly Glu Glu Leu
                325                 330                 335

Ala Leu Asp His Gln Asn Ser Pro Phe Leu Lys Pro Ser Val Asp Val
            340                 345                 350
```

| | | | | | | | | | | | | |
|---|---|---|---|---|---|---|---|---|---|---|---|---|
|Ser|Thr|Ala|His|Asn|Leu|Glu|Ala|Met|Leu|His|Leu|Leu|Asp|Gly|Tyr|
| | |355| | | |360| | | |365| | | | | |

| | | | | | | | | | | | | | | | |
|---|---|---|---|---|---|---|---|---|---|---|---|---|---|---|---|
|His|Gly|Lys|Gly|Glu|Arg|Phe|Val|Leu|Ser|Ser|Gly|Arg|Asp|His|Ala|
| |370| | | |375| | | |380| | | | | | |

His Gly Lys Gly Glu Arg Phe Val Leu Ser Ser Gly Arg Asp His Ala
        370                 375                 380

Leu Val Asn Lys Ala Ser Asp Phe Leu Lys His Leu Gln Ile Pro
385                 390                 395                 400

Pro Phe Trp Arg Gln Asp Ala Asn Lys Gly Met Val Arg Asn Ser Glu
                405                 410                 415

Gly Arg Trp Ile Gln Ala Glu Arg Leu Arg Phe Glu Asp His His Ser
            420                 425                 430

Pro Asp Ile His His His Leu Ser Gln Leu Arg Leu Asp His Pro Cys
            435                 440                 445

```
<210> SEQ ID NO 15
<211> LENGTH: 1167
<212> TYPE: DNA
<213> ORGANISM: Plant
<220> FEATURE:
<221> NAME/KEY: CDS
<222> LOCATION: (1)...(1044)

<400> SEQUENCE: 15
```

| | | | | | | | | | | | | | | | | |
|---|---|---|---|---|---|---|---|---|---|---|---|---|---|---|---|---|
|cgg|gtc|gac|cca|cgc|gtc|cgc|gaa|aac|gct|tcc|gac|tac|gag|gtt|gta|48|
|Arg|Val|Asp|Pro|Arg|Val|Arg|Glu|Asn|Ala|Ser|Asp|Tyr|Glu|Val|Val| |
|1| | | |5| | | | |10| | | | |15| | | aac ttc ctc tac gcc aca gct cgt gtt tct ctc ccc gaa ggt ttg ctt    96
Asn Phe Leu Tyr Ala Thr Ala Arg Val Ser Leu Pro Glu Gly Leu Leu
             20                  25                  30 ctc caa tca caa tca aga gat tct tgg gac cgt gag tct aac tgg ttt   144
Leu Gln Ser Gln Ser Arg Asp Ser Trp Asp Arg Glu Ser Asn Trp Phe
         35                  40                  45 ggc tac att gct gtc acg tct gat gaa cgg tct aag gct tta gga cgc   192
Gly Tyr Ile Ala Val Thr Ser Asp Glu Arg Ser Lys Ala Leu Gly Arg
     50                  55                  60 cgt gag atc tat ata gct ttg aga gga acg agc agg aac tat gag tgg   240
Arg Glu Ile Tyr Ile Ala Leu Arg Gly Thr Ser Arg Asn Tyr Glu Trp
 65                  70                  75                  80 gtc aat gtt ttg ggt gct agg cca act tca gct gac ccc ttg ctg cac   288
Val Asn Val Leu Gly Ala Arg Pro Thr Ser Ala Asp Pro Leu Leu His
                 85                  90                  95 gga ccc gag cag gat ggt tct ggt ggt gta gtt gaa ggt acg act ttt   336
Gly Pro Glu Gln Asp Gly Ser Gly Gly Val Val Glu Gly Thr Thr Phe
            100                 105                 110 gat agt gac agt gaa gat gaa gaa ggg tgt aag gtg atg ctc ggg tgg   384
Asp Ser Asp Ser Glu Asp Glu Glu Gly Cys Lys Val Met Leu Gly Trp
        115                 120                 125 ctc aca atc tat act tct aat cac ccc gaa tcg aaa ttc act aag ctg   432
Leu Thr Ile Tyr Thr Ser Asn His Pro Glu Ser Lys Phe Thr Lys Leu
    130                 135                 140 agt cta cgg tca cag ttg tta gcc aag atc aag gag ctt ctg ttg aag   480
Ser Leu Arg Ser Gln Leu Leu Ala Lys Ile Lys Glu Leu Leu Leu Lys
145                 150                 155                 160 tat aag gac gag aaa ccg agc att gtg ttg act gga cat agc ttg gga   528
Tyr Lys Asp Glu Lys Pro Ser Ile Val Leu Thr Gly His Ser Leu Gly
                165                 170                 175 cct aca gag gct gtt ctg gcc gcc tat gat ata gct gag aac ggt tcc   576
Pro Thr Glu Ala Val Leu Ala Ala Tyr Asp Ile Ala Glu Asn Gly Ser
            180                 185                 190 agt gat gat gtt ccg gtc act gct ata gtc ttt ggt tgt cca cag gta   624
Ser Asp Asp Val Pro Val Thr Ala Ile Val Phe Gly Cys Pro Gln Val -continued

```
                    195                 200                 205
gga aac aag gag ttc aga gac gaa gta atg agt cac aag aac tta aag       672
Gly Asn Lys Glu Phe Arg Asp Glu Val Met Ser His Lys Asn Leu Lys
        210                 215                 220 atc ctc cat gta agg aac acg att gat ctc tta act cga tac cca ggg       720
Ile Leu His Val Arg Asn Thr Ile Asp Leu Leu Thr Arg Tyr Pro Gly
225                 230                 235                 240 gga ctt tta ggg tat gtg gac ata gga ata aac ttt gtg atc gat aca       768
Gly Leu Leu Gly Tyr Val Asp Ile Gly Ile Asn Phe Val Ile Asp Thr
                245                 250                 255 aag aag tca ccg ttc cta agc gat tca agg aat cca ggg gat tgg cat       816
Lys Lys Ser Pro Phe Leu Ser Asp Ser Arg Asn Pro Gly Asp Trp His
        260                 265                 270 aat ctt cag gcg atg tta cat gtt gta gct gga tgg aat ggg aag aaa       864
Asn Leu Gln Ala Met Leu His Val Val Ala Gly Trp Asn Gly Lys Lys
            275                 280                 285 gga gag ttt aaa ctg atg gtt aag aga agt att gca tta gtg aac aag       912
Gly Glu Phe Lys Leu Met Val Lys Arg Ser Ile Ala Leu Val Asn Lys
290                 295                 300 tca tgc gag ttc ttg aaa gct gag tgt ttg gtg cca gga tct tgg tgg       960
Ser Cys Glu Phe Leu Lys Ala Glu Cys Leu Val Pro Gly Ser Trp Trp
305                 310                 315                 320 gta gag aag aac aaa gga ctg atc aag aac gaa gat ggt gaa tgg gtt      1008
Val Glu Lys Asn Lys Gly Leu Ile Lys Asn Glu Asp Gly Glu Trp Val
                325                 330                 335 ctt gct ccc gtt gaa gaa gaa cct gta cct gaa ttc taaattgtat           1054
Leu Ala Pro Val Glu Glu Glu Pro Val Pro Glu Phe
            340                 345 ttctgtattt ttctctaagg tcatgataaa tcaacaataa gcagttcaac tatgtgatga    1114
aaagacccaa gttattatat tgatatgagt ttatgagata aaaaaaaaaa aaa           1167

<210> SEQ ID NO 16
<211> LENGTH: 348
<212> TYPE: PRT
<213> ORGANISM: Plant

<400> SEQUENCE: 16

Arg Val Asp Pro Arg Val Arg Glu Asn Ala Ser Asp Tyr Glu Val Val
1               5                   10                  15

Asn Phe Leu Tyr Ala Thr Ala Arg Val Ser Leu Pro Glu Gly Leu Leu
            20                  25                  30

Leu Gln Ser Gln Ser Arg Asp Ser Trp Asp Arg Glu Ser Asn Trp Phe
        35                  40                  45

Gly Tyr Ile Ala Val Thr Ser Asp Glu Arg Ser Lys Ala Leu Gly Arg
50                  55                  60

Arg Glu Ile Tyr Ile Ala Leu Arg Gly Thr Ser Arg Asn Tyr Glu Trp
65                  70                  75                  80

Val Asn Val Leu Gly Ala Arg Pro Thr Ser Ala Asp Pro Leu Leu His
                85                  90                  95

Gly Pro Glu Gln Asp Gly Ser Gly Val Val Glu Gly Thr Thr Phe
            100                 105                 110

Asp Ser Asp Ser Glu Asp Glu Glu Gly Cys Lys Val Met Leu Gly Trp
        115                 120                 125

Leu Thr Ile Tyr Thr Ser Asn His Pro Glu Ser Lys Phe Thr Lys Leu
    130                 135                 140

Ser Leu Arg Ser Gln Leu Leu Ala Lys Ile Lys Glu Leu Leu Leu Lys
145                 150                 155                 160
```

-continued

```
Tyr Lys Asp Glu Lys Pro Ser Ile Val Leu Thr Gly His Ser Leu Gly
            165                 170                 175

Pro Thr Glu Ala Val Leu Ala Ala Tyr Asp Ile Ala Glu Asn Gly Ser
        180                 185                 190

Ser Asp Asp Val Pro Val Thr Ala Ile Val Phe Gly Cys Pro Gln Val
    195                 200                 205

Gly Asn Lys Glu Phe Arg Asp Glu Val Met Ser His Lys Asn Leu Lys
210                 215                 220

Ile Leu His Val Arg Asn Thr Ile Asp Leu Leu Thr Arg Tyr Pro Gly
225                 230                 235                 240

Gly Leu Leu Gly Tyr Val Asp Ile Gly Ile Asn Phe Val Ile Asp Thr
                245                 250                 255

Lys Lys Ser Pro Phe Leu Ser Asp Ser Arg Asn Pro Gly Asp Trp His
            260                 265                 270

Asn Leu Gln Ala Met Leu His Val Ala Gly Trp Asn Gly Lys Lys
        275                 280                 285

Gly Glu Phe Lys Leu Met Val Lys Arg Ser Ile Ala Leu Val Asn Lys
    290                 295                 300

Ser Cys Glu Phe Leu Lys Ala Glu Cys Leu Val Pro Gly Ser Trp Trp
305                 310                 315                 320

Val Glu Lys Asn Lys Gly Leu Ile Lys Asn Glu Asp Gly Glu Trp Val
                325                 330                 335

Leu Ala Pro Val Glu Glu Glu Pro Val Pro Glu Phe
            340                 345

<210> SEQ ID NO 17
<211> LENGTH: 195
<212> TYPE: PRT
<213> ORGANISM: Plant

<400> SEQUENCE: 17

Asp Tyr Glu Trp Val Asp Val Leu Gly Ala Arg Pro Asp Ser Ala Asp
1               5                   10                  15

Ser Leu Leu His Pro Lys Ser Leu Gln Lys Gly Ile Asn Asn Lys Asn
            20                  25                  30

Asp Glu Asp Glu Asp Glu Asp Glu Ile Lys Val Met Asp Gly
        35                  40                  45

Trp Leu Lys Ile Tyr Val Ser Ser Asn Pro Lys Ser Ser Phe Thr Arg
    50                  55                  60

Leu Ser Ala Arg Glu Gln Leu Gln Ala Lys Ile Glu Lys Leu Arg Asn
65                  70                  75                  80

Glu Tyr Lys Asp Glu Asn Leu Ser Ile Thr Phe Thr Gly His Ser Leu
                85                  90                  95

Gly Ala Ser Leu Ala Val Leu Ala Ser Phe Asp Val Val Glu Asn Gly
            100                 105                 110

Val Pro Val Asp Ile Pro Val Ser Ala Ile Val Phe Gly Ser Pro Gln
        115                 120                 125

Val Gly Asn Lys Ala Phe Asn Glu Arg Ile Lys Lys Phe Ser Asn Leu
    130                 135                 140

Asn Ile Leu His Val Lys Asn Lys Ile Asp Leu Ile Thr Leu Tyr Pro
145                 150                 155                 160

Ser Ala Leu Phe Gly Tyr Val Asn Ser Gly Ile Glu Leu Val Ile Asp
                165                 170                 175

Ser Arg Lys Ser Pro Ser Leu Lys Asp Ser Lys Asp Met Gly Asp Trp
```

His Asn Leu
    195

<210> SEQ ID NO 18
<211> LENGTH: 1344
<212> TYPE: DNA
<213> ORGANISM: Plant
<220> FEATURE:
<221> NAME/KEY: CDS
<222> LOCATION: (1)...(1344)

<400> SEQUENCE: 18

| | | |
|---|---|---|
| atg acg gcg gaa gat att cgc cgg cga gat aaa aaa acc gaa gaa gaa<br>Met Thr Ala Glu Asp Ile Arg Arg Arg Asp Lys Lys Thr Glu Glu Glu<br>1               5                   10                  15 | | 48 |
| aga aga cta aga gac acg tgg cgt aag atc caa gga gaa gac gat tgg<br>Arg Arg Leu Arg Asp Thr Trp Arg Lys Ile Gln Gly Glu Asp Asp Trp<br>            20                  25                  30 | | 96 |
| gcc ggg tta atg gat cca atg gat cca att ctt aga tcg gag cta atc<br>Ala Gly Leu Met Asp Pro Met Asp Pro Ile Leu Arg Ser Glu Leu Ile<br>        35                  40                  45 | | 144 |
| cgt tac ggc gaa atg gct caa gct tgt tac gac gct ttc gat ttc gat<br>Arg Tyr Gly Glu Met Ala Gln Ala Cys Tyr Asp Ala Phe Asp Phe Asp<br>50                  55                  60 | | 192 |
| ccc gct tcc aaa tac tgc ggc acc tcc agg ttc acg cga ctc gag ttc<br>Pro Ala Ser Lys Tyr Cys Gly Thr Ser Arg Phe Thr Arg Leu Glu Phe<br>65                  70                  75                  80 | | 240 |
| ttc gat tct ctc gga atg atc gat tcc ggt tac gag gtg gcg cgt tac<br>Phe Asp Ser Leu Gly Met Ile Asp Ser Gly Tyr Glu Val Ala Arg Tyr<br>                85                  90                  95 | | 288 |
| ctc tac gcg acg tcg aac atc aat ctc ccg aac ttc ttc tcg aaa tcg<br>Leu Tyr Ala Thr Ser Asn Ile Asn Leu Pro Asn Phe Phe Ser Lys Ser<br>            100                 105                 110 | | 336 |
| cgg tgg tct aaa gtc tgg agc aaa aac gct aat tgg atg gga tac gtc<br>Arg Trp Ser Lys Val Trp Ser Lys Asn Ala Asn Trp Met Gly Tyr Val<br>        115                 120                 125 | | 384 |
| gcc gtt tca gac gac gaa acg tct cgt aac cga ctc ggc cgc cgt gat<br>Ala Val Ser Asp Asp Glu Thr Ser Arg Asn Arg Leu Gly Arg Arg Asp<br>130                 135                 140 | | 432 |
| atc gcg att gcg tgg aga gga acc gtt acg aaa ctt gaa tgg atc gcg<br>Ile Ala Ile Ala Trp Arg Gly Thr Val Thr Lys Leu Glu Trp Ile Ala<br>145                 150                 155                 160 | | 480 |
| gat cta aag gat tat tta aaa ccg gta acc gaa aac aag atc cga tgc<br>Asp Leu Lys Asp Tyr Leu Lys Pro Val Thr Glu Asn Lys Ile Arg Cys<br>                165                 170                 175 | | 528 |
| ccc gac ccg gcc gtt aaa gtc gaa tcc gga ttc tta gat ctc tac act<br>Pro Asp Pro Ala Val Lys Val Glu Ser Gly Phe Leu Asp Leu Tyr Thr<br>            180                 185                 190 | | 576 |
| gac aaa gac aca acc tgc aaa ttc gcg aga ttc tca gcg cgt gaa cag<br>Asp Lys Asp Thr Thr Cys Lys Phe Ala Arg Phe Ser Ala Arg Glu Gln<br>        195                 200                 205 | | 624 |
| att tta acg gag gtg aaa cgg tta gtg gaa gaa cac ggc gac gac gat<br>Ile Leu Thr Glu Val Lys Arg Leu Val Glu Glu His Gly Asp Asp Asp<br>210                 215                 220 | | 672 |
| gat tcc gat tta agc atc acc gtg acg gga cac agt ctc ggc ggc gcg<br>Asp Ser Asp Leu Ser Ile Thr Val Thr Gly His Ser Leu Gly Gly Ala<br>225                 230                 235                 240 | | 720 |
| tta gcg ata tta agc gcg tac gat ata gcg gag atg aga ttg aat cgg<br>Leu Ala Ile Leu Ser Ala Tyr Asp Ile Ala Glu Met Arg Leu Asn Arg<br>                245                 250                 255 | | 768 |

```
agt aag aaa ggg aaa gtg att ccg gtg acg gtg ttg aca tac gga gga      816
Ser Lys Lys Gly Lys Val Ile Pro Val Thr Val Leu Thr Tyr Gly Gly
            260                 265                 270 ccg aga gtt ggg aac gtt agg ttt agg gag agg atg gag gaa ttg gga      864
Pro Arg Val Gly Asn Val Arg Phe Arg Glu Arg Met Glu Glu Leu Gly
        275                 280                 285 gtg aaa gtg atg aga gta gtg aat gtt cac gac gtg gtt ccc aag tcg      912
Val Lys Val Met Arg Val Val Asn Val His Asp Val Val Pro Lys Ser
    290                 295                 300 ccg gga ttg ttt ttg aac gag agt aga cct cac gcg ctg atg aag ata      960
Pro Gly Leu Phe Leu Asn Glu Ser Arg Pro His Ala Leu Met Lys Ile
305                 310                 315                 320 gcg gag ggg ttg ccg tgg tgt tat agc cac gtg ggg gag gag ctg gcg     1008
Ala Glu Gly Leu Pro Trp Cys Tyr Ser His Val Gly Glu Glu Leu Ala
                325                 330                 335 ttg gat cat cag aac tcg ccg ttt ctt aaa cct tcc gtt gat gtt tct     1056
Leu Asp His Gln Asn Ser Pro Phe Leu Lys Pro Ser Val Asp Val Ser
            340                 345                 350 act gct cat aat ctt gaa gct atg ctt cat tta ctt gac ggg tat cat     1104
Thr Ala His Asn Leu Glu Ala Met Leu His Leu Leu Asp Gly Tyr His
        355                 360                 365 gga aaa gga gag aga ttt gtg ctg tcg agt ggg aga gac cat gcg cta     1152
Gly Lys Gly Glu Arg Phe Val Leu Ser Ser Gly Arg Asp His Ala Leu
    370                 375                 380 gtg aac aaa gcg tcg gac ttt ttg aaa gag cat tta caa att cca ccg     1200
Val Asn Lys Ala Ser Asp Phe Leu Lys Glu His Leu Gln Ile Pro Pro
385                 390                 395                 400 ttt tgg cgt caa gac gcg aat aaa gga atg gtt cgg aac agt gaa ggt     1248
Phe Trp Arg Gln Asp Ala Asn Lys Gly Met Val Arg Asn Ser Glu Gly
                405                 410                 415 cgt tgg att caa gcc gag cgt ctc cgt ttt gag gat cat cat tct cct     1296
Arg Trp Ile Gln Ala Glu Arg Leu Arg Phe Glu Asp His His Ser Pro
            420                 425                 430 gat atc cac cac cat ctc tct cag ctc cgt ctt gat cat cct tgt taa     1344
Asp Ile His His His Leu Ser Gln Leu Arg Leu Asp His Pro Cys *
        435                 440                 445

<210> SEQ ID NO 19
<211> LENGTH: 447
<212> TYPE: PRT
<213> ORGANISM: Plant

<400> SEQUENCE: 19

Met Thr Ala Glu Asp Ile Arg Arg Arg Asp Lys Lys Thr Glu Glu Glu
1               5                   10                  15

Arg Arg Leu Arg Asp Thr Trp Arg Lys Ile Gln Gly Glu Asp Asp Trp
            20                  25                  30

Ala Gly Leu Met Asp Pro Met Asp Pro Ile Leu Arg Ser Glu Leu Ile
        35                  40                  45

Arg Tyr Gly Glu Met Ala Gln Ala Cys Tyr Asp Ala Phe Asp Phe Asp
    50                  55                  60

Pro Ala Ser Lys Tyr Cys Gly Thr Ser Arg Phe Thr Arg Leu Glu Phe
65                  70                  75                  80

Phe Asp Ser Leu Gly Met Ile Asp Ser Gly Tyr Glu Val Ala Arg Tyr
                85                  90                  95

Leu Tyr Ala Thr Ser Asn Ile Asn Leu Pro Asn Phe Phe Ser Lys Ser
            100                 105                 110

Arg Trp Ser Lys Val Trp Ser Lys Asn Ala Asn Trp Met Gly Tyr Val
```

```
            115                 120                 125
Ala Val Ser Asp Asp Glu Thr Ser Arg Asn Arg Leu Gly Arg Arg Asp
    130                 135                 140

Ile Ala Ile Ala Trp Arg Gly Thr Val Thr Lys Leu Glu Trp Ile Ala
145                 150                 155                 160

Asp Leu Lys Asp Tyr Leu Lys Pro Val Thr Glu Asn Lys Ile Arg Cys
                165                 170                 175

Pro Asp Pro Ala Val Lys Val Glu Ser Gly Phe Leu Asp Leu Tyr Thr
            180                 185                 190

Asp Lys Asp Thr Thr Cys Lys Phe Ala Arg Phe Ser Ala Arg Glu Gln
        195                 200                 205

Ile Leu Thr Glu Val Lys Arg Leu Val Glu Glu His Gly Asp Asp Asp
    210                 215                 220

Asp Ser Asp Leu Ser Ile Thr Val Thr Gly His Ser Leu Gly Gly Ala
225                 230                 235                 240

Leu Ala Ile Leu Ser Ala Tyr Asp Ile Ala Glu Met Arg Leu Asn Arg
                245                 250                 255

Ser Lys Lys Gly Lys Val Ile Pro Val Thr Val Leu Thr Tyr Gly Gly
            260                 265                 270

Pro Arg Val Gly Asn Val Arg Phe Arg Glu Arg Met Glu Glu Leu Gly
        275                 280                 285

Val Lys Val Met Arg Val Val Asn Val His Asp Val Val Pro Lys Ser
    290                 295                 300

Pro Gly Leu Phe Leu Asn Glu Ser Arg Pro His Ala Leu Met Lys Ile
305                 310                 315                 320

Ala Glu Gly Leu Pro Trp Cys Tyr Ser His Val Gly Glu Glu Leu Ala
                325                 330                 335

Leu Asp His Gln Asn Ser Pro Phe Leu Lys Pro Ser Val Asp Val Ser
            340                 345                 350

Thr Ala His Asn Leu Glu Ala Met Leu His Leu Leu Asp Gly Tyr His
        355                 360                 365

Gly Lys Gly Glu Arg Phe Val Leu Ser Ser Gly Arg Asp His Ala Leu
    370                 375                 380

Val Asn Lys Ala Ser Asp Phe Leu Lys Glu His Leu Gln Ile Pro Pro
385                 390                 395                 400

Phe Trp Arg Gln Asp Ala Asn Lys Gly Met Val Arg Asn Ser Glu Gly
                405                 410                 415

Arg Trp Ile Gln Ala Glu Arg Leu Arg Phe Glu Asp His His Ser Pro
            420                 425                 430

Asp Ile His His His Leu Ser Gln Leu Arg Leu Asp His Pro Cys
        435                 440                 445

<210> SEQ ID NO 20
<211> LENGTH: 27
<212> TYPE: DNA
<213> ORGANISM: Artificial Sequence
<220> FEATURE:
<223> OTHER INFORMATION: Primer

<400> SEQUENCE: 20
atgtctagag aagatattgc gcggcga                              27

<210> SEQ ID NO 21
<211> LENGTH: 28
<212> TYPE: DNA
<213> ORGANISM: Artificial Sequence
```

-continued

```
<220> FEATURE:
<223> OTHER INFORMATION: Primer

<400> SEQUENCE: 21
gatgagctcg acgaagctga gagagatg                                          28
```